United States Patent [19]
Park et al.

[11] Patent Number: 6,087,366
[45] Date of Patent: *Jul. 11, 2000

[54] USE OF FLAVOPIRIDOL OR A PHARMACEUTICALLY ACCEPTABLE SALT THEREOF FOR INHIBITING CELL DAMAGE OR CELL DEATH

[75] Inventors: David S. Park; Stephen E. Farinelli; Lloyd A. Greene, all of New York, N.Y.

[73] Assignee: The Trustees of Columbia University in the City of New York, New York, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/613,242

[22] Filed: Mar. 7, 1996

[51] Int. Cl.$^7$ ............................. A01N 43/90; A01N 43/42
[52] U.S. Cl. ........................... 514/263; 514/285; 514/302
[58] Field of Search ................... 514/285, 302, 514/263

[56] References Cited

U.S. PATENT DOCUMENTS

| | | | |
|---|---|---|---|
| 2,921,070 | 1/1960 | Da Re et al. ........................ | 260/274.2 |
| 3,810,896 | 5/1974 | White et al. ...................... | 260/268 BC |
| 3,816,466 | 6/1974 | Strandtmann et al. .............. | 260/345.2 |
| 4,550,115 | 10/1985 | Nardi et al. .............................. | 514/320 |
| 4,871,742 | 10/1989 | Bonne et al. ............................ | 514/262 |
| 4,886,806 | 12/1989 | Walenta et al. ......................... | 514/253 |
| 4,900,727 | 2/1990 | Kattige et al. ............................ | 514/212 |
| 5,013,852 | 5/1991 | Walenta et al. .......................... | 549/362 |
| 5,238,954 | 8/1993 | Aristoff et al. .......................... | 514/456 |
| 5,403,842 | 4/1995 | Leonardi et al. ........................ | 514/252 |

FOREIGN PATENT DOCUMENTS 9503293 2/1995 WIPO .

OTHER PUBLICATIONS

Brooks, S.F. et al., (1993). Apoptosis induced by NGF–withdrawal from differentiated PC12 cells involves activation of p34$^{cdc2}$ kinase. *Society For Neuroscience Abstracts*, 19: 885.
Farinelli, S.E. et al., (1993). A possible link between the cell cycle and apoptosis of PC12 cells. *Society For Neuroscience*.
Abstracts , 19: 885.
Ferrari, G. and Greene, L.A. (1993). Proliferative inhibition by dominant–negative Ras rescues naive and neuronally differentiated PC12 cells from death. *The Embo Journal*, 13: 5922–5928.
Kaur, G. et al., (1992). Growth inhibition with reversible cell cycle arrest of carcinoma cells by flavone L86–8275. *Journal of The National Cancer Institute*, 84: 1736–1740.
Losiewicz, M.D. et al., (1994). Potent inhibition of Cdc2 kinase by the flavanoid L86–8275. *Biochemical and Biophysical Research Communication*, 201: 589–595 and;.
Worland, P.J. et al., (1993). Alteration of the phosphorylation states of p34$^{cdc2}$ kinase by the flavone L86–8275 in breast carcinoma cells. *Biochemical Pharmacology*, 46: 1831–1840.

*Primary Examiner*—Theodore J. Criares
*Attorney, Agent, or Firm*—John P. White; Cooper & Dunham LLP

[57] ABSTRACT

Flavopiridol and its salts are used to inhibit neuronal cell damage or neuronal cell death.

16 Claims, 20 Drawing Sheets

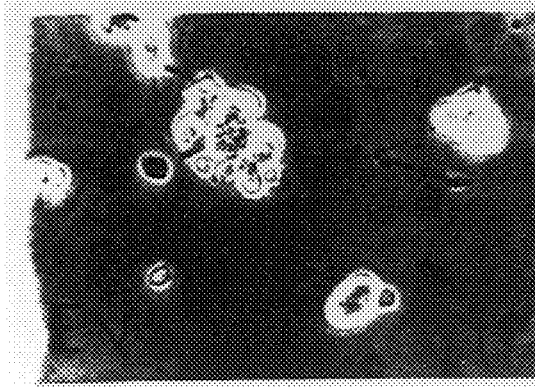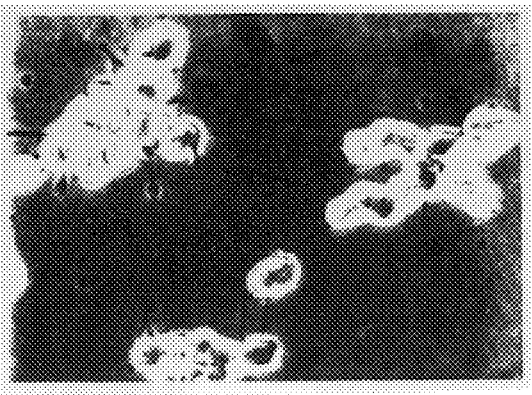

USE OF FLAVOPIRIDOL OR A PHARMACEUTICALLY ACCEPTABLE SALT THEREOF FOR INHIBITING CELL DAMAGE OR CELL DEATH

The invention disclosed herein was made with Government support under NIH Grant No. NS 33689-01 from the Department of Health and Human Services. Accordingly, the U.S. Government has certain rights in this invention.

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

BACKGROUND OF THE INVENTION

Neuronal apoptosis is an important aspect of nervous system development and a component of neuronal injury and disease. The most generally accepted model of the developmental regulation of neuronal death states that limiting quantities of target-derived neurotrophic support control the optimum number of neuron-target interactions (1). Neurotrophins also play a role in ameliorating the effects of oxidative stress and many forms of neuronal injury (2,3).

In an effort to define the mechanisms of neurotrophin action in neuronal survival, two model systems, the PC12 pheochromocytoma cell line and cultured primary sympathetic neurons, have been exploited. The PC12 cell line was initially derived from a rat adrenal medullary pheochromocytoma (4). When grown in serum-containing medium, PC12 cells divide and resemble precursors of adrenal chromaffin cells and sympathetic neurons. Upon addition of NGF, these "naive" cells, gradually attain the phenotypic properties of sympathetic neurons. Both naive and neuronally-differentiated PC12 cells undergo apoptosis upon removal of trophic support (i.e. serum or serum/NGF) (5,6). The response of PC12 cells to withdrawal of trophic support is quite analogous to that of sympathetic neurons. In vivo (7–9) and in vitro (10,11) evidence demonstrate that sympathetic neurons require NGF for survival. Studies (6,12,13,14) have shown that both PC12 cells and sympathetic neurons undergo apoptotic death upon NGF deprivation.

Although the mechanisms by which neurotrophins suppress apoptosis are not fully understood, it has been hypothesized that neurotrophins prevent apoptotic death by acting to coordinate cell cycle progression and/or prevent inappropriate cell cycle reentry (12,15–17). Accordingly, this hypothesis predicts that cells which attempt to enter or traverse the cell cycle without a set of proper mitogenic signals will undergo apoptosis. In support of this model, numerous observations of apoptosis in the presence of conflicting cell cycle signals have been reported in non-neuronal systems (18–21). The cell cycle/apoptosis hypothesis was applied to interpret the characteristics of apoptotic death in PC12 cells, sympathetic neurons, and other cells of neuronal origin (15). In this view, withdrawal of serum from naive, proliferating PC12 cells leads to an uncoordinated and disastrous attempt to continue to cycle, whereas in post-mitotic differentiated PC12 cells and sympathetic neurons, withdrawal of NGF results in an inappropriate attempt to reenter the cell cycle and consequent death.

Previous findings have provided some evidence for this interpretation and for the cell cycle/apoptosis model in neuronal cells. While apoptotic death of sympathetic neurons and post-mitotic PC12 cells is delayed by protein synthesis inhibitors (11,14,23), such inhibitors do not block cell death of naive PC12 cells (24). One interpretation of this discrepancy is that the proteins needed for apoptosis are regulators of the general cell cycle mechanism. Since naive PC12 cells continually synthesize cell cycle proteins, they may utilize a preexisting pool of cell cycle regulators to enter the cell cycle even in the absence of new protein synthesis. Without appropriate coordinating mitogenic signals such as provided by growth factors, apoptosis would result. In contrast, post-mitotic cells would require de novo synthesis of cell cycle proteins prior to inappropriate cell cycle reentry. In accordance with this view, Freeman et al. (17) showed that NGF removal from sympathetic neurons results in an induction of the cell cycle regulatory protein cyclin D1 along with transcription factors, c-fos and c-jun (25), typically induced prior to cell division. Furthermore, the activation of another cell cycle protein, cdc2, has been reported in differentiated PC12 cells as a consequence of NGF withdrawal (26). It has also been reported that expression of SV40 T antigen in Purkinje cells results in apoptotic death (27) concurrent with DNA synthesis.

Initial attempts to test the cell cycle/apoptosis model by blocking cell cycle progression have produced additional support for this hypothesis. Induction of dominant-negative ras expression in both naive and post-mitotic PC12 cells inhibits cell cycle progression and death induced by withdrawal of trophic support (15). A similar correlation between survival and blockade of cell cycle has been shown in PC12 cells and sympathetic neurons treated with N-acetyl cysteine (NAC) (28). In these cases, the mechanisms by which the cell cycle is inhibited are unknown.

The cyclin dependent kinase (cdk) family, which among others includes cdk2-4/6, and cdc2 (cdk1), is an important group of cell cycle regulatory molecules whose inhibition represents a more defined means to block cell cycle progression or reentry. cdc2 is a well characterized M-phase regulator and may also serve to mediate progression through the S-phase (30). cdk2 and 3 activities are required for progression through the G1/S phases of the cycle (30,31). The present invention discloses the effects of inhibitors of the cdk family of kinases on PC12 cells and sympathetic neurons after withdrawal of trophic factor.

SUMMARY OF THE INVENTION

The present invention provides a method of inhibiting neuronal cell damage or neuronal cell death in a subject comprising administering to the subject flavopiridol (see FIG. 10) or a pharmaceutically acceptable salt thereof, the flavopiridol or salt thereof being present in an amount effective to inhibit neuronal cell damage or neuronal cell death in the subject.

The present invention also provides a pharmaceutical composition comprising flavopiridol or a pharmaceutically acceptable salt thereof in an amount effective to inhibit neuronal cell damage or neuronal cell death, and a pharmaceutically acceptable carrier.

BRIEF DESCRIPTION OF THE FIGURES

FIGS. 4A, 4B, 4C, 4D, 4E, and 4F show phase contrast micrographs of neuronally differentiated PC12 cells maintained in serum-free medium for two days and treated with the following: (A) no additives; (B) NGF, 100 ng/ml; (C) flavopiridol, 1 $\mu$M; (D) flavopiridol, 1 $\mu$M+NGF; (E) olomoucine, 200 $\mu$M; (F) olomoucine, 200 $\mu$M+NGF. Magnification is 375×.

DETAILED DESCRIPTION OF THE INVENTION

Figure 10:
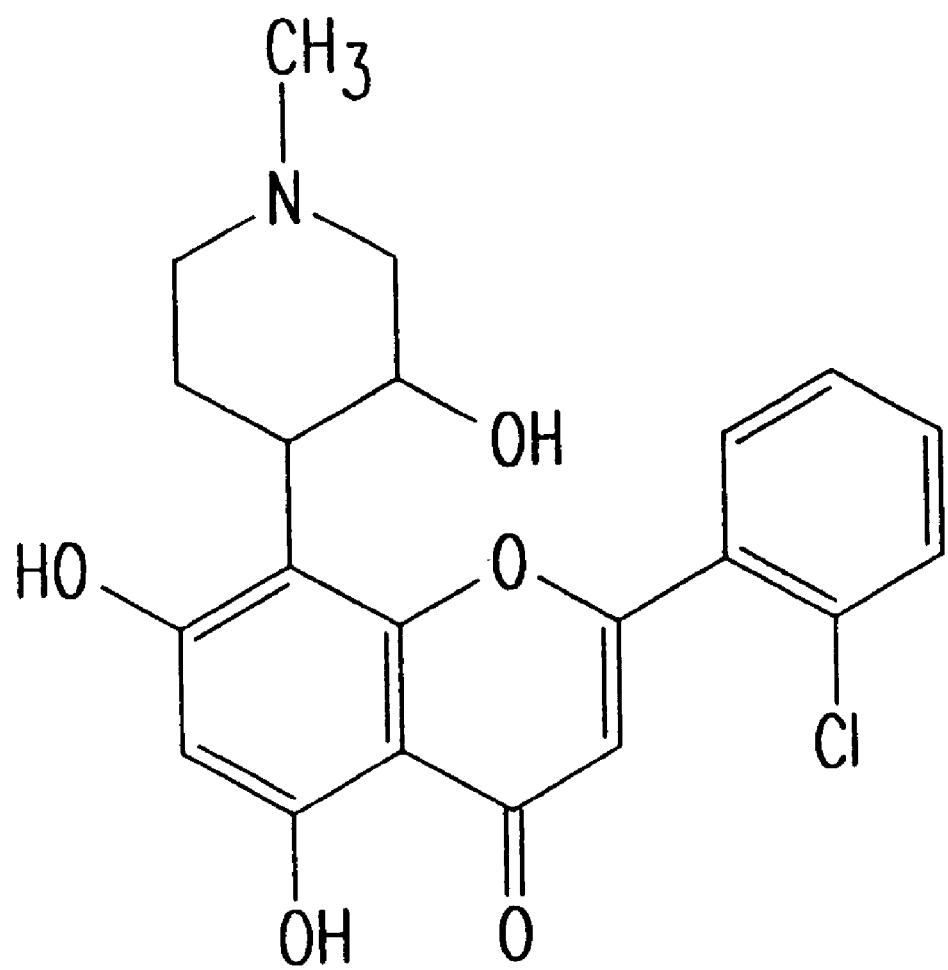
FIG. 10 shows the chemical structure of flavopiridol, also known as [(−) cis-5,7-dihydroxy-2-(2-chlorophenyl)-8[4-(3hydroxy-1-methyl)-piperidinyl]-4H-benzopyran-4-one] or L86-8275.

The present invention provides a method of inhibiting cell damage or cell death in a subject comprising administering to the subject flavopiridol (see FIG. 10) or a pharmaceutically acceptable salt thereof, the flavopiridol or salt thereof being present in an amount effective to inhibit cell damage or cell death in the subject.

In one embodiment of the invention, the cell damage or cell death is neuronal cell damage or cell death.

In another embodiment of the invention, the subject is a mammal such as a human or a mouse.

In yet another embodiment of the invention, the neuronal cell damage or neuronal cell death is associated with a traumatic injury.

The term "traumatic injury" is used herein to designate a physical injury that severs or damages nerve fibers.

In another embodiment of the invention, the neuronal cell damage or neuronal cell death is associated with a stroke.

In yet another embodiment of the invention, the neuronal cell damage or neuronal cell death is associated with a neurological disorder In another embodiment of the invention, the neurological disorder is selected from the group consisting of Parkinson's disease, amyotrophic lateral sclerosis, and Alzheimer's disease.

In yet another embodiment of the invention, the effective amount of flavopiridol or salt thereof is from about 5 mg/Kg of body weight to about 50 mg/Kg of body weight per day.

In another embodiment of the invention, wherein the effective amount of flavopiridol or salt thereof is from about 10 mg/Kg of body weight to about 20 mg/Kg of body weight per day.

In another embodiment of the invention, the flavopiridol or salt thereof is administered orally, intravenously, subcutaneously, intramuscularly, topically, parenterally, by inhalation, rectally, or intraocularly.

The present invention also provides a pharmaceutical composition comprising flavopiridol or a pharmaceutically acceptable salt thereof in an amount effective to inhibit cell damage or cell death, and a pharmaceutically acceptable carrier.

In one preferred embodiment the pharmaceutical carrier may be a liquid and the pharmaceutical composition would be in the form of a solution. In another equally preferred embodiment, the pharmaceutically acceptable carrier is a solid and the composition is in the form of a powder or tablet. In a further embodiment, the pharmaceutical carrier is a gel and the composition is in the form of a suppository or cream. In a further embodiment the active ingredient may be formulated as a part of a pharmaceutically acceptable transdermal patch.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The active ingredient may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

The active ingredient can be administered orally in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The active ingredient can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

In one embodiment of the invention, the cell damage or cell death is neuronal cell damage or cell death.

In another embodiment of the invention, the neuronal cell damage or neuronal cell death is associated with a traumatic injury.

In yet another embodiment of the invention, the neuronal cell damage or neuronal cell death is associated with a stroke.

In another embodiment of the invention, the neuronal cell damage or neuronal cell death is associated with a neurological disorder.

In yet another embodiment of the invention, the neurological disorder is selected from the group consisting of Parkinson's disease, amyotrophic lateral sclerosis, and Alzheimer's disease.

In another embodiment of the invention, the effective amount of flavopiridol or salt thereof is from about 200 mg to about 7500 mg.

In yet another embodiment of the invention, the effective amount of flavopiridol or salt thereof is from about 400 mg to about 3000 mg.

This invention will be better understood from the Experimental Details which follow. However, one skilled in the art will readily appreciate that the specific methods and results discussed are merely illustrative of the invention as described more fully in the claims which follow thereafter.

Experimental Details

Experimental Procedures

Materials

Human recombinant NGF was kindly provided by Genentech. Flavopiridol (L86-8275, [(−) cis-5,7-dihydroxy-2-(2-chlorophenyl) -8[4-(3-hydroxy-1-methyl) -piperidinyl]-4H-benzopyran-4-one]) and PD98059 were generous gifts from Dr. Peter Worland (National Institute of Health) and Parke Davis Pharmaceuticals, respectively. Olomoucine (2-(2- hydroxyethylamino) -6-benzylamino-9-methylpurine) and iso-olomoucine was purchased from LC laboratories. Flavopiridol and olomoucine/iso-olomoucine were dissolved in DMSO as stock solutions at 50 mM and 200 mM, respectively. Mouse NGF and anti-mouse NGF antiserum were obtained from Sigma Chemical Co.

PC12 cell culture

Naive PC12 cells were cultured and passaged as previously described (4) in collagen-coated dishes with RPMI 1640 medium supplemented with 10% heat inactivated horse serum and 5% fetal bovine serum. Neuronally-differentiated PC12 cells were obtained by washing PC12 cells and replating them onto collagen-coated dishes at approximately 1–2×10 cells/100 mm dish in the presence of 100 ng/ml NGF for a period of 8–9 days in serum-free RPMI 1640.

PC12 cell survival assay

For survival experiments, naive or neuronally-differentiated PC12 cells were washed extensively in serum-, NGF-free medium as previously described (6,24) and replated onto collagen-coated 24-well tissue culture dishes at a density of approximately $2 \times 10^5$ cells per well. The final volume of medium in each well, including all drugs was 1 ml. To allow time for blockade of DNA synthesis, naive PC12 cells were, in some cases, pretreated with drug for 16 hr prior to serum withdrawal. NGF-treated neuronally-differentiated cells were not pretreated with drug prior to serum deprivation. At appropriate times of culture under the desired conditions, cells were lysed and the numbers of viable cells were determined as previously described (24). The number of intact nuclei was determined by counting in a hemacytometer. All counts were performed in triplicate, and survival data are expressed as a percentage of cells plated on day 0+/−SEM.

Culture and survival assay of rat sympathetic neurons

Primary cultures of rat sympathetic neurons were obtained from dissociated superior cervical ganglia of postnatal day 1 rats (strain, Sprague Dawly) as described previously (32). The cells were plated in 0.5 ml of medium per well in collagen-coated 24-well dishes at a density of approximately 0.5 ganglia per well. The growth medium was RPMI 1640 medium supplemented with 10% heat-inactivated horse serum and 60 ng/ml mouse NGF. To eliminate non-neuronal cells, a mixture of uridine and 5-fluorodeoxyuridine (10 $\mu$M each) were added to the cultures on the following day. On the third day after plating, the neurons were deprived of NGF by washing the cultures three times with RPMI 1640 medium containing 10% heat-inactivated horse serum. The appropriate drug and/or NGF or anti-mouse NGF antibody (1:200 dilution) was added in a final volume of 0.5 ml of the same medium described above. At appropriate times, the numbers of viable, phase bright neurons were determined by strip counting as previously described (33). All survival data are expressed as relative to the original number of cells counted for each well. All experimental points were performed in triplicate and are reported as mean+/−SEM,

[$^3$H]-thymidine incorporation

Naive PC12 cells were plated in collagen-coated 24-well dishes at a density of $4 \times 10^5$ per well in RPMI 1640 medium containing 3 $\mu$M insulin (Sigma) or 10% horse serum and 5% fetal calf serum. The drugs tested were equally effective in inhibiting thymidine incorporation in either culture condition. The cells were pretreated with the appropriate drug for a period of 16 hr prior to the addition of 1 $\mu$Ci per well of [$^3$H]-thymidine (NEN Products, Dupont). The cells were exposed to thymidine for 1–2 hour and then washed three times with cold PBS. Each well was extracted with 1 ml of 10% TCA at 4° C. for 1 hr, and the insoluble material was solubilized overnight at room temperature with 0.3 ml 1N NaOH. After neutralization with an equal volume of 1 N HCl, the solution was quantified by scintillation counting. The level of background counts was determined by treating cells with 10 $\mu$M aphidicolin. All experimental points were performed in triplicate. All data are presented relative to untreated control samples as mean+/−SEM.

Determination of rate of protein synthesis

Neuronally-differentiated PC12 cells and sympathetic neurons were plated on 24-well dishes as described above. After the cultures were pretreated with the appropriate drug for 1 hr, 5 $\mu$Ci [$^3$H]-leucine was added per well and the cells were allowed to incorporate the isotope for 10 hr. The cultures were washed and prepared for scintillation counting as described above for thymidine incorporation. Background levels of radioactivity was determined by treating wells with 5 $\mu$g/ml cycloheximide. All experimental points were performed in triplicate and the data are presented relative to untreated control samples as mean+/−SEM.

Determination of c-Jun kinase activity c-Jun kinase (JNK) was affinity purified from PC12 cell extracts with GST-c-Jun (a gift from Dr. Michael Karin, University of California, San Diego) bound to GSH-agarose beads (Sigma) by methods previously described (34). c-Jun kinase activity was determined by an in vitro solid-phase kinase assay as described previously (34). Activated c-Jun kinase was isolated from PC12 cells treated with 0.5 mM sodium arsenite for 30 min. To determine the potential inhibitory effects of flavopiridol and olomoucine on c-Jun-kinase activity in vitro, the indicated concentrations of inhibitor were added to constant amounts of activated c-Jun kinase during the solid-phase kinase assay. In vivo effects of the CDK inhibitors on c-Jun kinase activation following NGF withdrawal from neuronally-differentiated PC12 cells was determined by treatment of NGF-deprived cell cultures with flavopiridol or olomoucine for various times, affinity purification of c-Jun kinase activity from the cell extract (normalized for protein content as quantified by the Biorad Protein assay), and determination of c-Jun kinase activity as described above. GST-c-Jun was resolved on a 8.5% SDS gel and incorporation of $^{32}PO_4$ was quantified by autoradiography and densitometry.

Results

The cdk inhibitors flavopiridol and olomoucine are effective in blocking death of trophic-factor-deprived, post-mitotic PC12 cells and sympathetic neurons, but not of dividing PC12 cells.

The CDK inhibitors flavopiridol and olomoucine inhibit PC12 cell cycle progression and death of post-mitotic, neuronally-differentiated PC12 cells Two cdk inhibitors were utilized to study the effects of cell cycle blockade on survival of PC12 cells and sympathetic neurons. Flavopiridol was first reported to inhibit immunoprecipitated cdk1 activity from breast carcinoma cells with an $IC_{50}$ of approximately 0.4 $\mu$M (assayed at an ATP concentration of 375 $\mu$M) (35). Subsequently, this flavanoid derivative was demonstrated to inhibit the G1/S phase related cdk2/4 enzymes with similar potency. In addition, Kaur et al. (36) reported that flavopiridol blocks progression from both G1 to S and G2 to M in several breast carcinoma cell lines. Flavopiridol has been shown to be a relatively poor inhibitor of all other protein kinases examined including cAMP-dependent protein kinase, EGF receptor kinase, and PKC (35). Olomoucine, a purine derivative, has been demonstrated to be a relatively specific inhibitor for cdk1/2/5 and ERK1/MAP-kinase activities (37). Examination of approximately thirty other protein kinases revealed that olomoucine had poor inhibitory actions on these enzymes (37). Tests of the cell cycle inhibitory actions of this agent on 60 tumor cell lines demonstrated that olomoucine arrests cells at both the G1 to S and G2 to M borders (37).

Figure 1A:
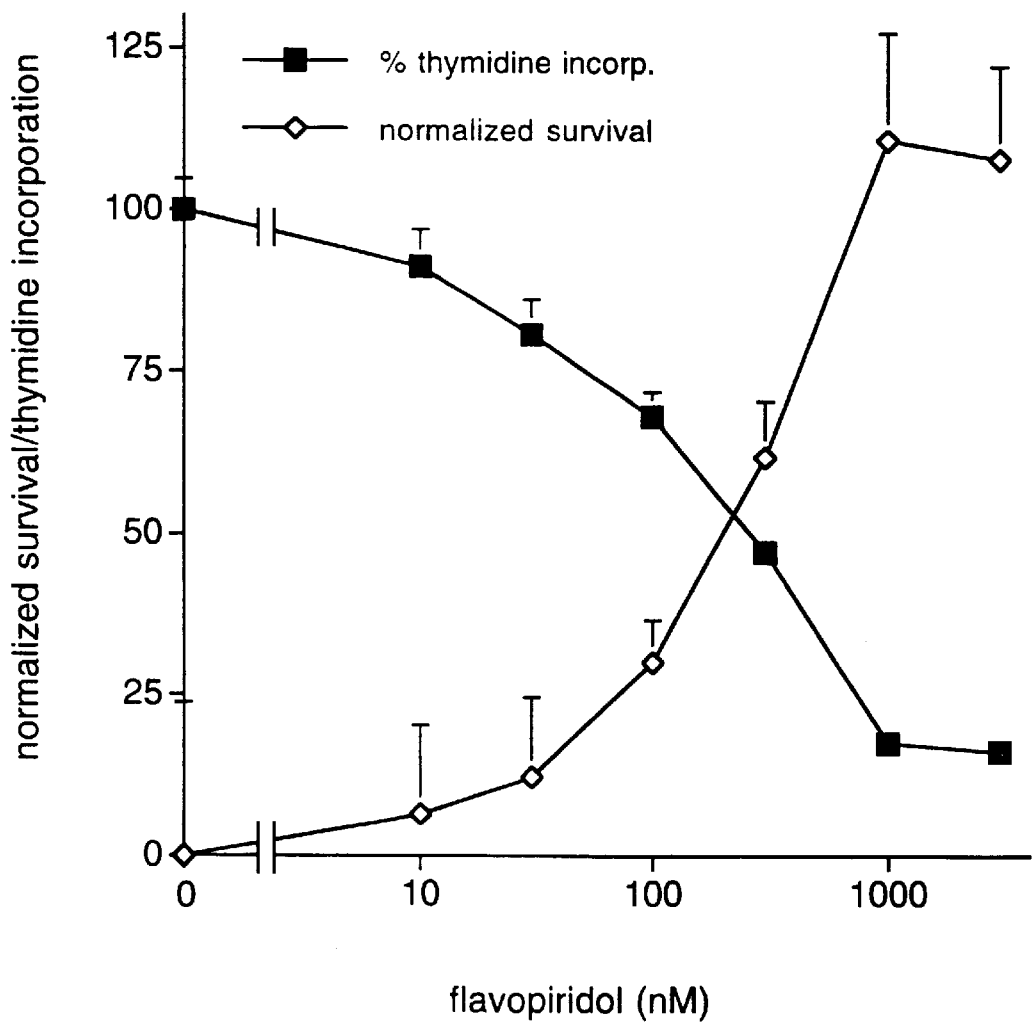
FIGS. 1A and 1B show that flavopiridol inhibits [$^3$H] thymidine incorporation by dividing PC12 cells and promotes survival of neuronally-differentiated PC12 cells in serum-free medium following withdrawal of NGF. The neuronal PC12 cell phenotype was obtained by treatment with NGF in serum free medium for 8 days. (A) Relationship between the dose of drug required for promotion of day 2 survival of NGF-deprived neuronally-differentiated PC12 cells and inhibition of thymidine incorporation by dividing NGF-untreated (naive) PC12 cells. Naive PC12 cells were pretreated with the indicated concentrations of flavopiridol for 16 hours in serum- or insulin-containing RPMI 1640 medium prior to measurement of thymidine incorporation (determined as described in Experimental Procedures). Cell survival data are normalized so that survival without flavopiridol (51%) is defined as zero and 100% survival is defined as the number of cells initially present. (B) Effect of flavopiridol (3 $\mu$M) on the time course of survival of neuronally-differentiated PC12 cells following withdrawal of NGF. Each data point is the mean±SEM of 3 samples.
Figure 2A:
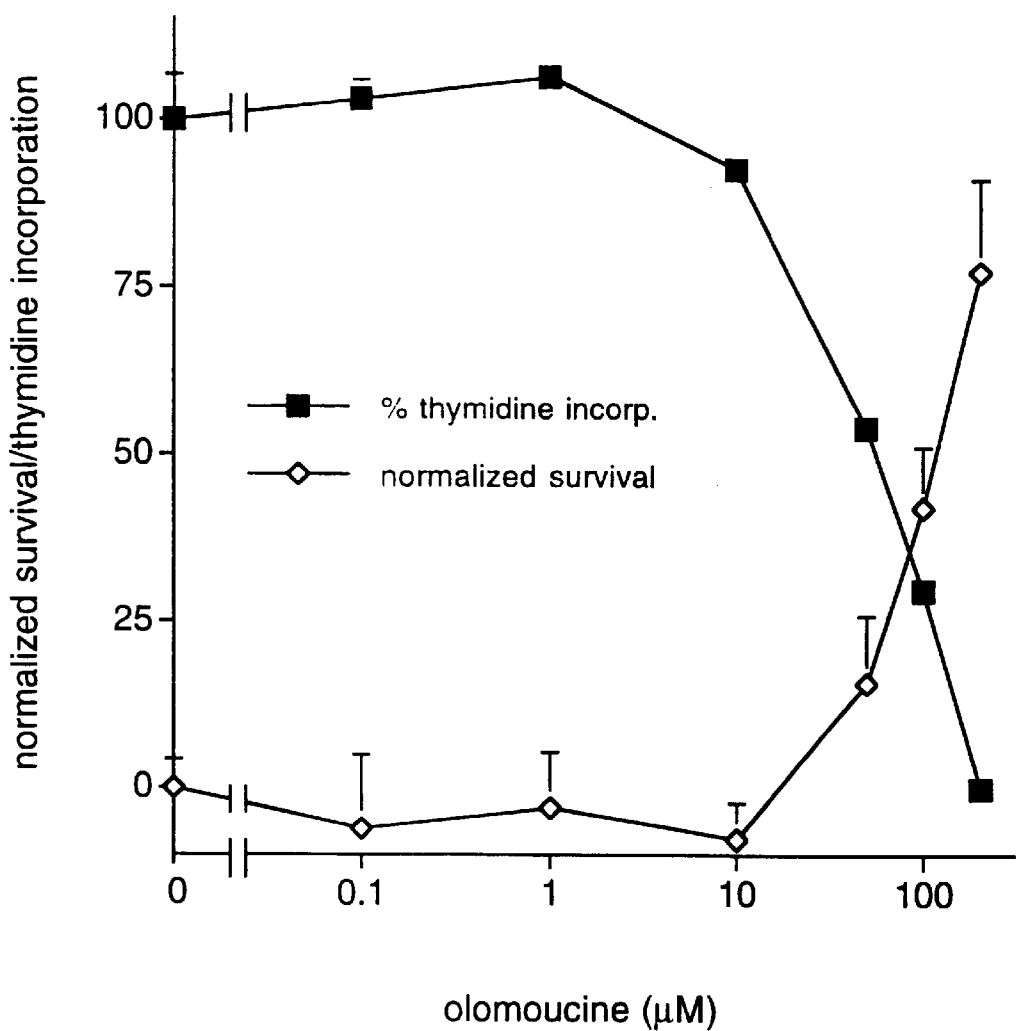
FIGS. 2A and 2B show that olomoucine inhibits [H] thymidine incorporation by dividing PC12 cells and promotes survival of neuronally-differentiated PC12 cells in serum-free medium following withdrawal of NGF. (A) Relationship between the dose of drug required for promotion of day 2 survival of NGF-deprived neuronally-differentiated PC12 cells and inhibition of thymidine incorporation by naive PC12 cells. Naive PC12 cells were pretreated with the indicated concentrations of olomoucine for 16 hours in serum- or insulin-containing medium prior to measurement of thymidine incorporation. Cell survival data are normalized so that survival without olomoucine (43%) is defined as zero and 100% survival is defined as the number of cells initially present. (B) Effect of olomoucine (200 $\mu$M) on the time course of survival of neuronally-differentiated PC12 cells following withdrawal of NGF. Each data point is the mean±SEM of 3 samples.

First, it was determined whether these inhibitors inhibit DNA synthesis by naive PC12 cells. As shown in FIGS. 1A and 2A, flavopiridol and olomoucine inhibited [$^3$H]-thymidine incorporation with $IC_{50}$ values of approximately 0.3 µM and 100 µM respectively.

Figure 1B:
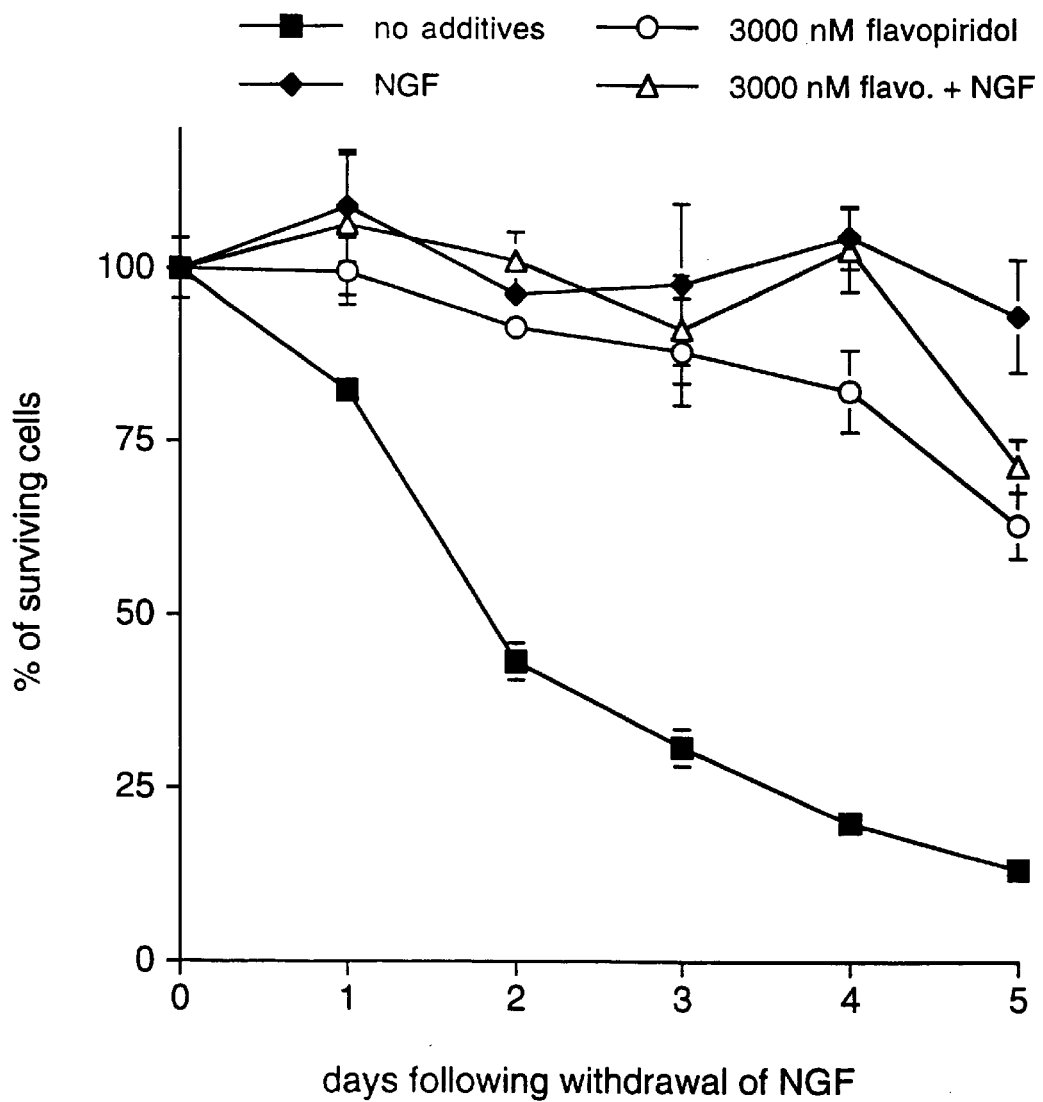
Figure 2B:
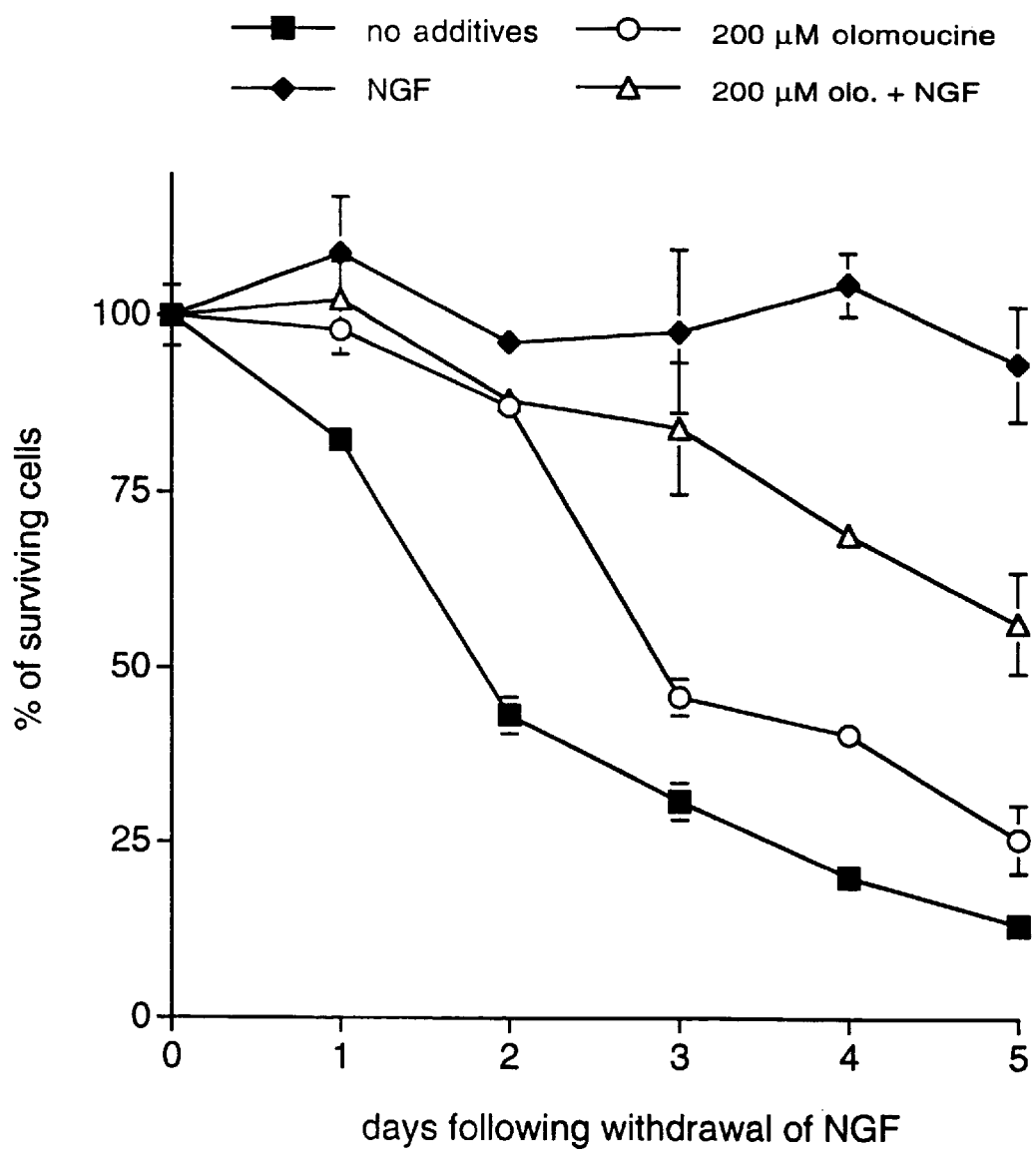

Next, the ability of flavopiridol and olomoucine to block death induced by NGF withdrawal from PC12 cells that had been neuronally differentiated by pre-exposure to NGF in serum-free medium was determined. Maximal protection was observed at a concentration of 1 µM for flavopiridol and 200 µM for olomoucine. Flavopiridol was more effective at long-term protection of NGF-differentiated PC12 cells than olomoucine with good maintenance of survival even 5 days after NGF withdrawal (FIGS. 1B and 2B). Both drugs showed progressive toxicity even in the presence of NGF which appears to limit their long-term efficacy. As shown in FIGS. 1A, 1B, 2A, and 2B, both drugs significantly delayed death, and this correlated well with inhibition of thymidine incorporation.

Figure 3A:
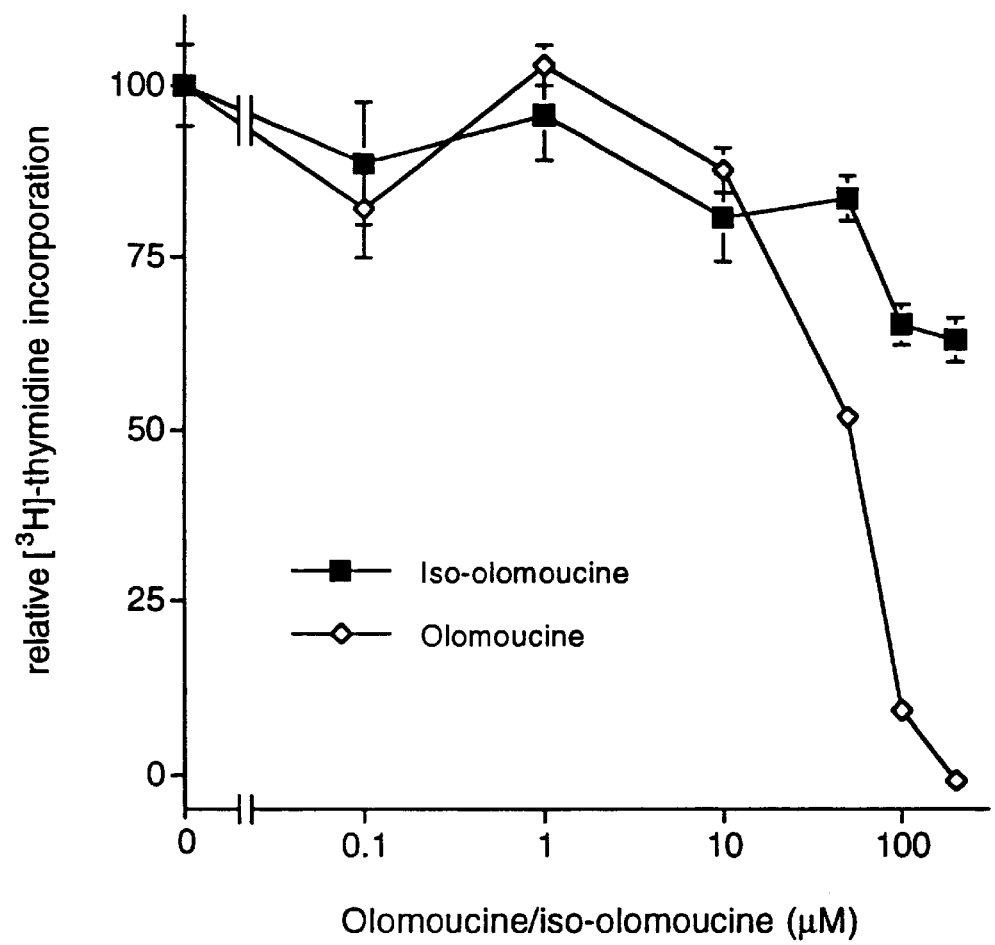
FIGS. 3A and 3B show that iso-olomoucine is less effective than olomoucine at inhibiting [$^3$H]-thymidine incorporation and maintaining survival of neuronally-differentiated PC12 cells following withdrawal of NGF. (A) Comparison of inhibition of thymidine incorporation by olomoucine and iso-olomoucine. Naive PC12 cells were pretreated with the indicated concentrations of olomoucine/iso-olomoucine for 16 hours in serum- or insulin-containing medium prior to measurement of thymidine incorporation. (B) Time course of survival of neuronally-differentiated PC12 cells following withdrawal of NGF. Each data point is the mean±SEM of 3 samples.
Figure 3B:
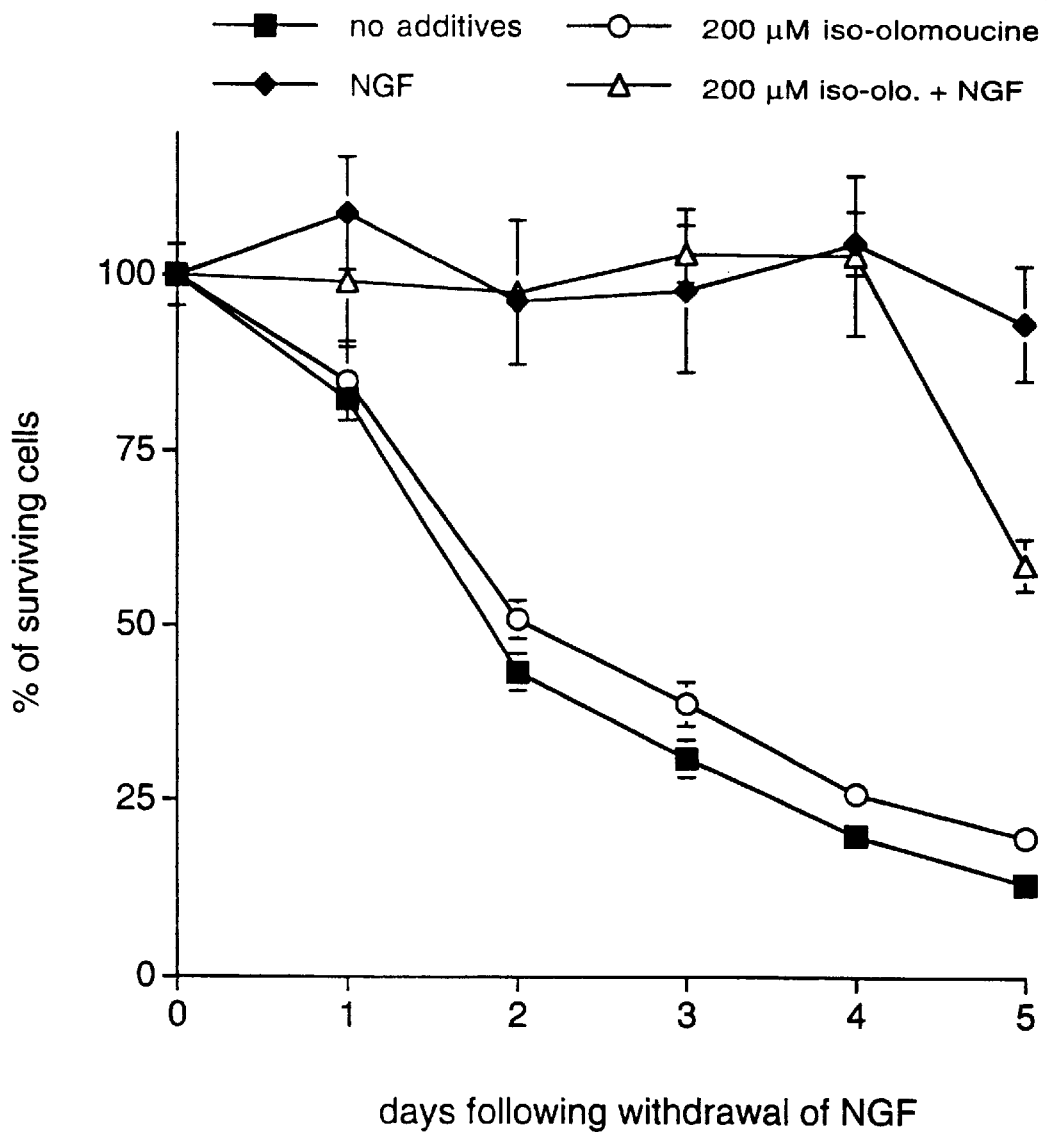
Figure 4A:
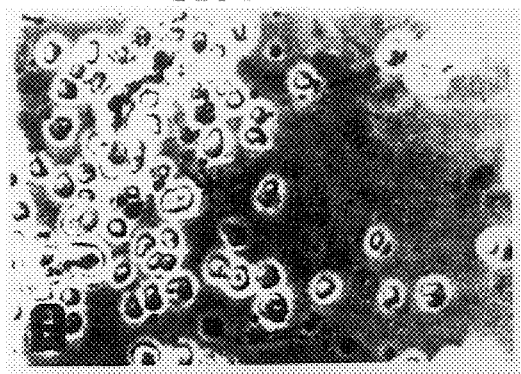
Figure 4B:
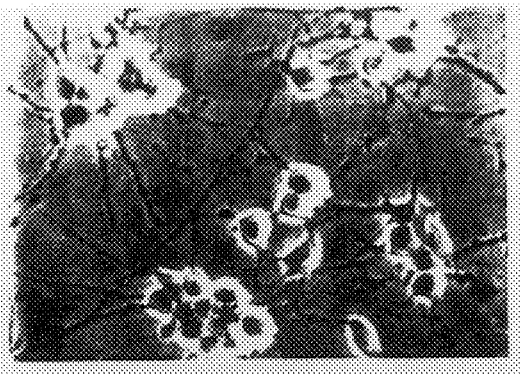
Figure 4C:
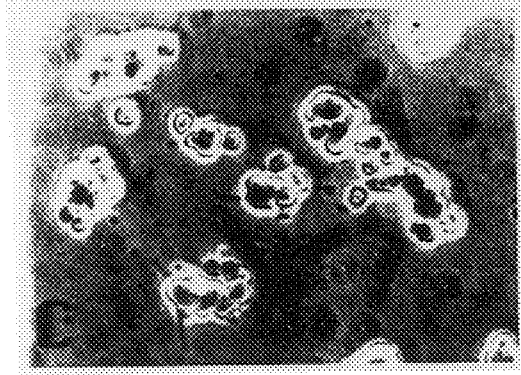
Figure 4D:

As a control for non-specific effects of olomoucine, the analog iso-olomoucine was also tested for its ability to inhibit cell cycle progression and neuronal death. This derivative is identical to olomoucine with the exception of the location of a substituent methyl group on the imidazole ring of the purine backbone. This change severely reduces inhibition of cdk1 activity ($IC_{50}$>500 µM, iso-olomoucine vs $IC_{50}$=7 µM, olomoucine). As shown in FIGS. 3A and 3B, iso-olomoucine was far less effective than olomoucine in inhibiting both thymidine incorporation and cell death.

FIGS. 4A, 4B, 4C, 4D, 4E, and 4F show the morphology of neuronally-differentiated PC12 cells treated with the cdk inhibitors in serum-free medium with and without NGF. The cells rescued by the drugs showed the typical phase-bright morphology of living cells but did not regenerate neurites. In the presence of NGF, the drugs appeared to partially suppress neurite regeneration. Potential reasons for this effect on regeneration include inhibition of cdk5, a kinase linked to neurite formation (38,39) and/or of ERK1 kinase, activation of which also appears to be required for neurite outgrowth (40). Olomoucine is reported to inhibit GST-ERK1 activity in vitro ($IC_{50}$=30 µM).

To test whether ERK inhibition by olomoucine might contribute to its actions on survival (by either promoting or blocking death), naive and neuronally-differentiated PC12 cells were treated with PD 098059 (20–100 µM), an inhibitor of the MEK kinase which mediates NGF-promoted activation of ERKs (41). The behavior of the cells was examined when passaged into serum-free medium with or without NGF. Although the drug effectively suppressed NGF-stimulated neurite regeneration (as anticipated from its inhibition of ERK activation), it neither blocked nor mimicked the capacity of NGF to promote survival of naive or neuronally-differentiated PC12 cells. These findings suggest that inhibition of ERK activity does not account for either the survival-promoting actions of olomoucine in the absence of NGF, nor for its toxicity in the presence of NGF. They also indicate that ERK activation is not required for NGF-promoted survival.

Figure 5A:
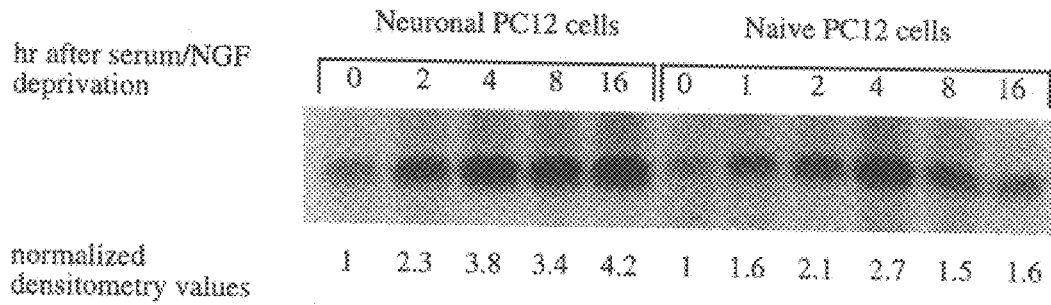
FIGS. 5A, 5B, and 5C show the effects of flavopiridol and olomoucine on JNK activity. JNK activity was determined using GST-c-Jun protein as substrate as described in METHODS. (A) Neuronally-differentiated PC12 cultures (lane 1–5) or naive PC12 cells (lane 6–11) were deprived of serum or NGF respectively for the indicated times. The densitometric values at each time point are normalized such that the 0 time point is defined as 1. (B) Neuronally-differentiated PC12 cultures were deprived of NGF in the presence or absence of the flavopiridol or olomoucine for the indicated times. The densitometric values at each time point are normalized such that the 0 time point is defined as 1. (C) Constant amounts of activated JNK activity were assayed in vitro in the presence or absence of the indicated concentrations of flavopiridol (fl) or olomoucine (olo). The densitometric values at each concentration of inhibitor is normalized such that the JNK activity at time 0 in the absence of drug is defined as 1.

Flavopiridol and olomoucine do not prevent the activation of c-Jun kinase activity in NGF-deprived neuronally-differentiated PC12 cells Recent findings suggest that activation or activity of Jun kinase (JNK) family members may be involved in apoptosis of NGF-deprived sympathetic neurons and PC12 cells (42). In accordance with these findings, c-Jun kinase activity increases in both naive and neuronally-differentiated PC12 cells upon withdrawal of trophic support (FIG. 5A). In naive PC12 cells, JNK activity peaks at 4 hr after serum withdrawal at a level approximately two to three-fold higher than in control cells cultured in the presence of serum and then declines thereafter. JNK activity also peaks at 4 hr after NGF deprivation of neuronally-differentiated PC12 cells. Unlike naive serum-deprived PC12 cultures, however, the level of kinase activity in NGF-deprived neuronally-differentiated cells remains elevated for at least 16 hr.

Figure 5B:
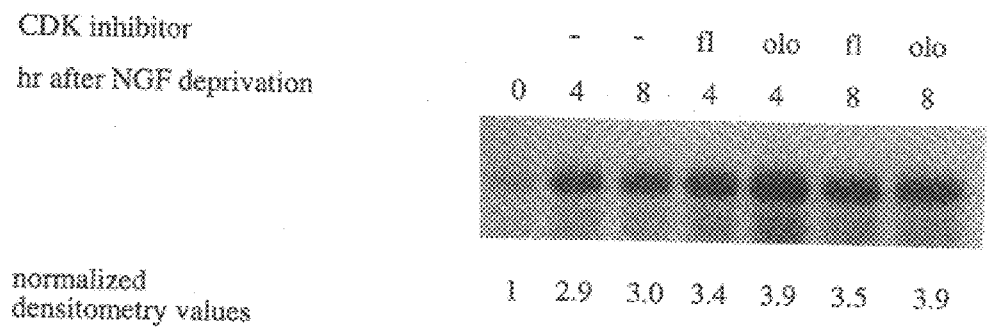

The ability of flavopiridol and olomoucine to promote survival of neuronal PC12 cells by preventing the induction of JNK activity through the JNK-specific MAP kinase cascade was examined (see 43 for review). As shown in FIG. 5B, treatment of neuronal PC12 cultures with either flavopiridol (1 µM) or olomoucine (200 µM) did not decrease the level of JNK activation that occurred in vivo when the cells were deprived of NGF.

Figure 5C:
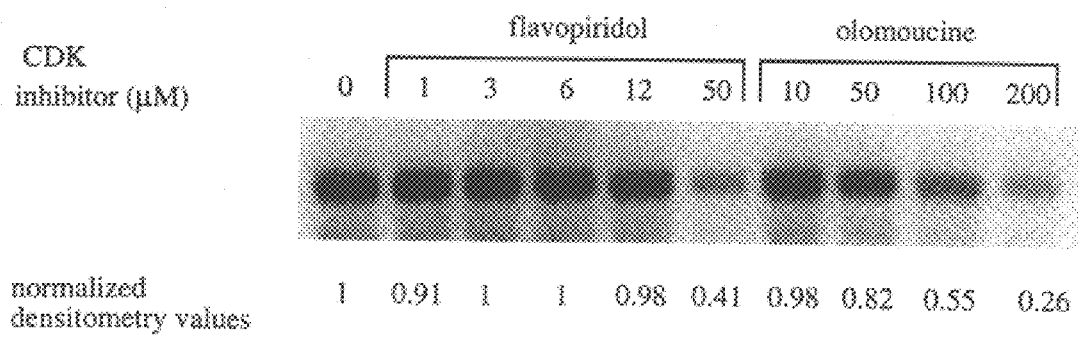

The ability of CDK inhibitors to directly affect JNK activity in vitro was investigated. At concentrations similar to that at which it promotes survival in culture, olomoucine inhibited direct phosphorylation of GST-c-jun by activated JNK in vitro. As shown in FIG. 5C, olomoucine inhibited GST-c-Jun phosphorylation with an $IC_{50}$ of approximately 100 µM. In contrast, a 12 µM concentration of flavopiridol (12-fold higher than that required for survival of neuronal cultures) had no effect on the in vitro phosphorylation of GST-c-Jun, while 50 µM flavopiridol significantly inhibited phosphorylation (FIG. 5C). These observations indicate that it is unlikely that the CDK inhibitors used here promote survival by preventing activation of JNK and that at least flavopiridol does not work by inhibiting JNK activity.

Flavopiridol and olomoucine prevent death of NGF-deprived sympathetic neurons

Figure 6A:
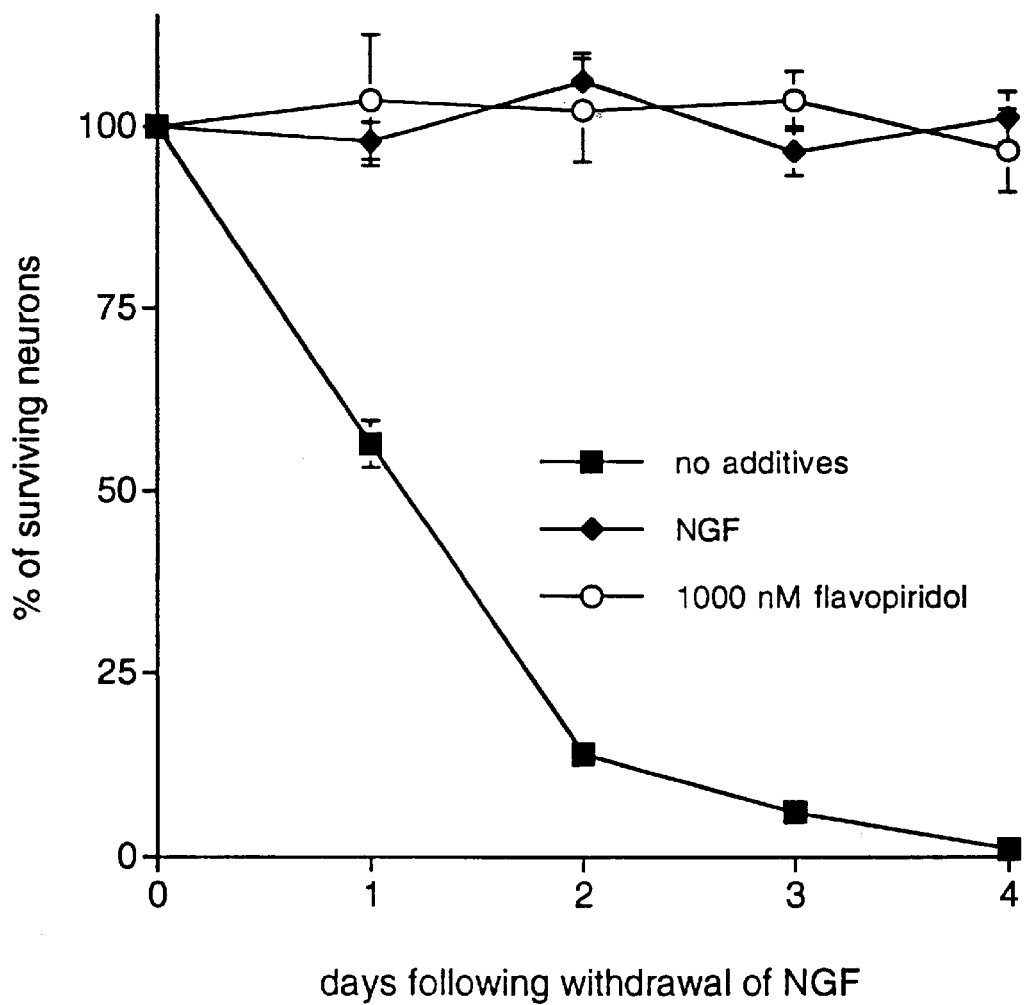
FIGS. 6A, 6B, 6C, and 6D show that flavopiridol and olomoucine promote the survival of rat sympathetic neurons following withdrawal of NGF whereas iso-olomoucine does not. Primary cultures of neonatal rat superior cervical ganglion neurons were grown in the presence of NGF for three days prior to withdrawal. Concurrent with withdrawal of NGF, the cultures were treated with the appropriate agents. Each data point is the mean±SEM of 3 samples and is expressed relative to the number of neurons present in each well at the time of NGF withdrawal. (A) Effects of flavopiridol (1 $\mu$M) on the time course of survival of sympathetic neurons after withdrawal of NGF. (B) Effects of various doses of flavopiridol on day 2 survival of NGF-deprived sympathetic neurons. (C) Effects of olomoucine and iso-olomoucine (200 $\mu$M) on the time course of survival of sympathetic neurons after withdrawal of NGF. (D) Effect of various doses of olomoucine on day 2 survival of NGF-deprived sympathetic neurons.
Figure 6B:
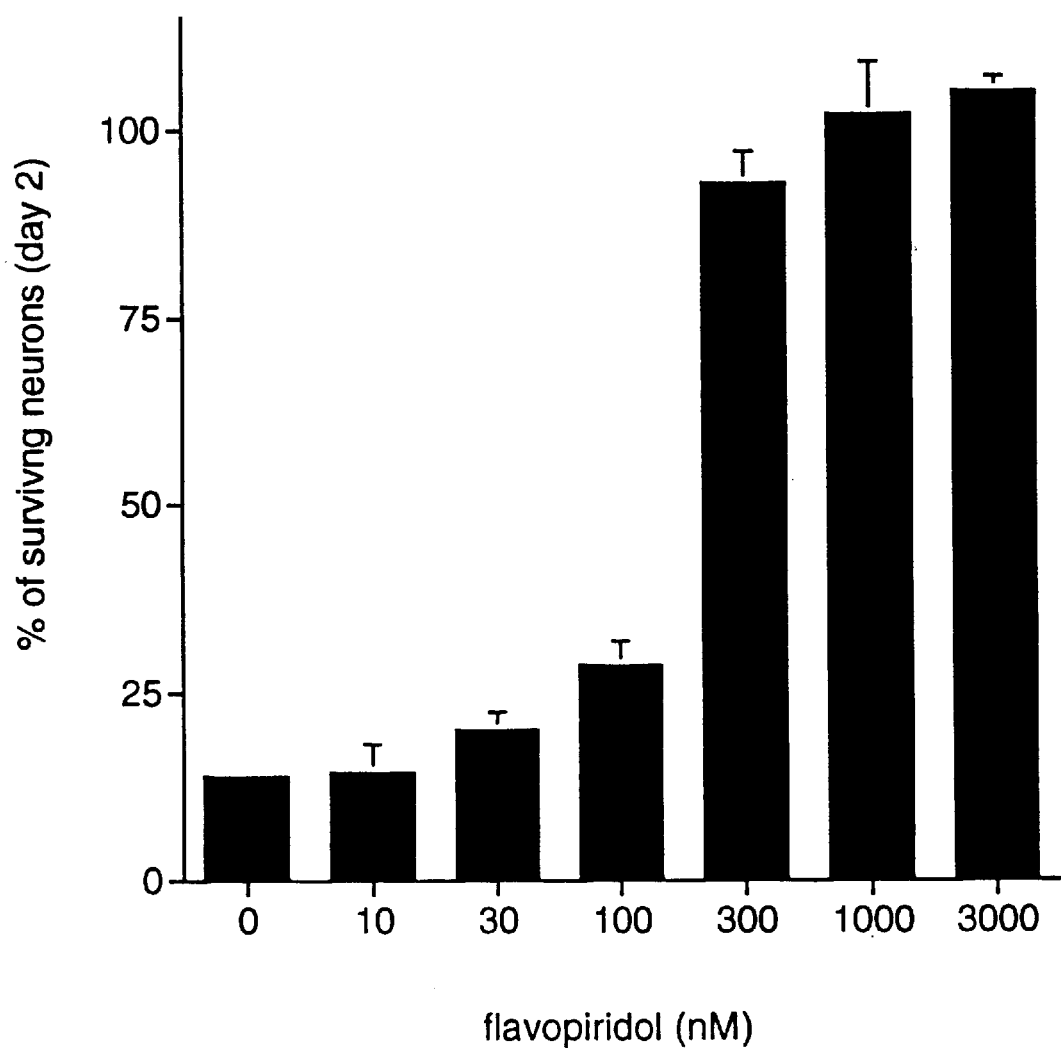
Figure 6C:
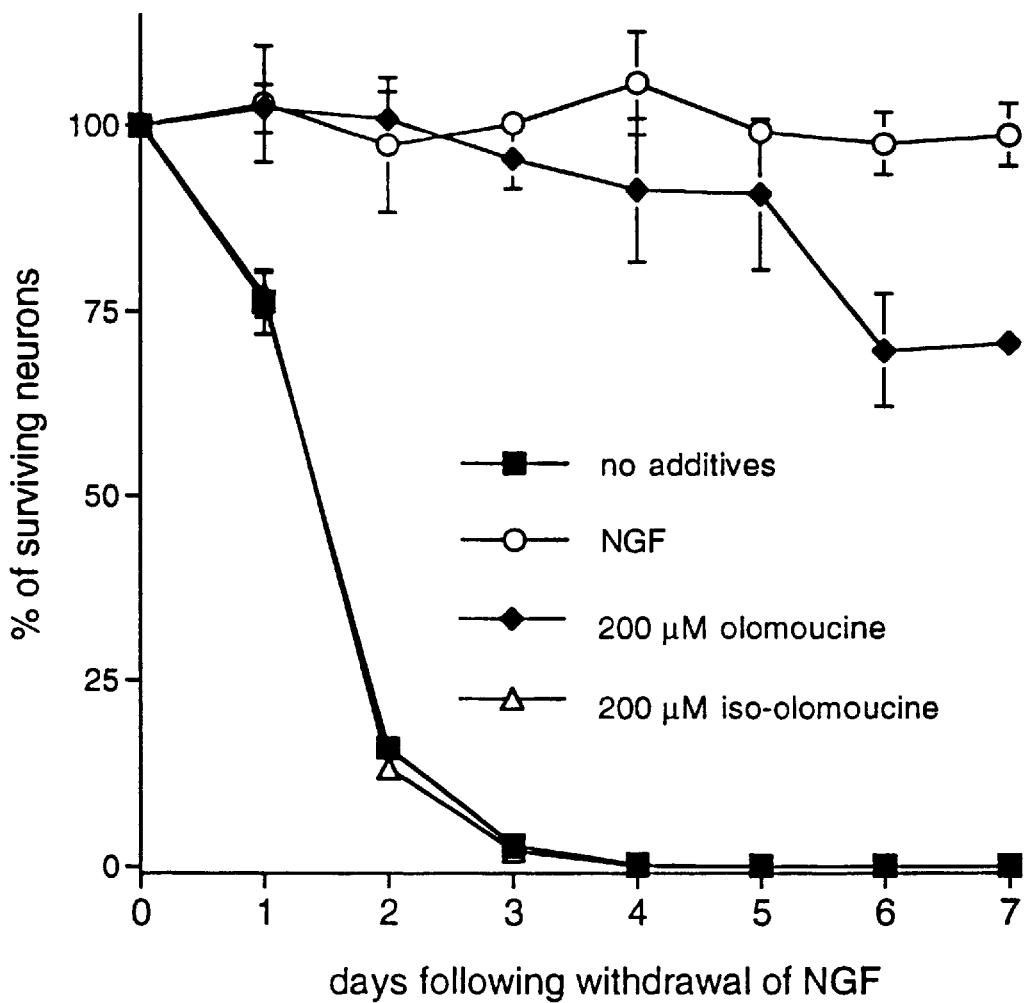
Figure 6D:
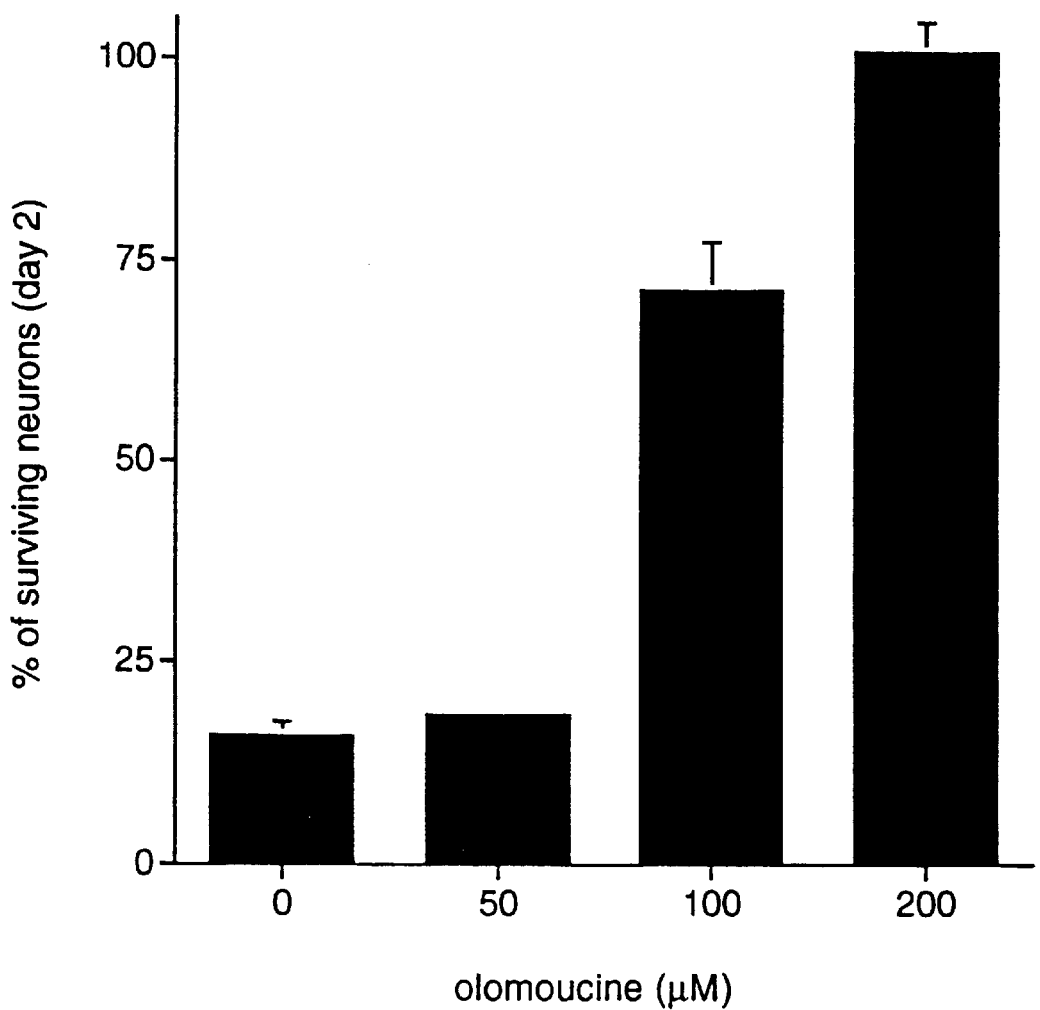
Figure 7A:
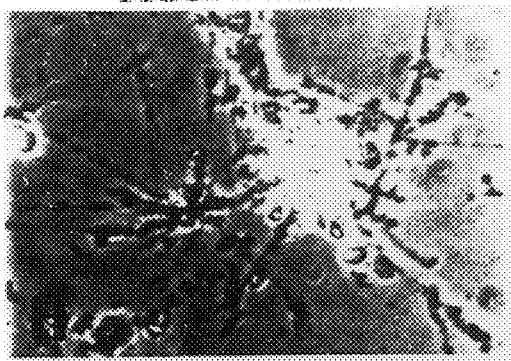
FIGS. 7A, 7B, 7C, 7D, 7E, and 7F show phase contrast micrographs of rat sympathetic neurons maintained in NGF-free medium for various times and treated with the following: (A) no additives, day 2; (B) NGF, day 2; (C) flavopiridol, 1 $\mu$M, day 2; (D) flavopiridol, 1 $\mu$M, day 6; (E) olomoucine, 200 $\mu$M, day 2; (F) olomoucine, 200 $\mu$M, day 6; Magnification is 375×.
Figure 7B:
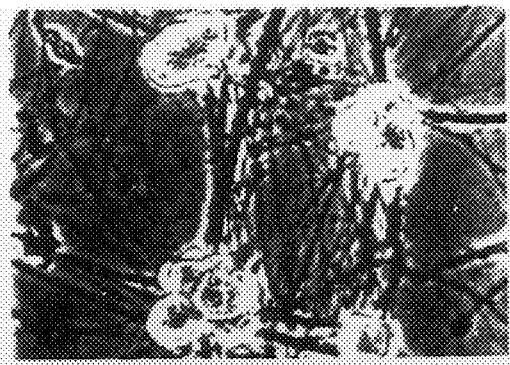
Figure 7C:
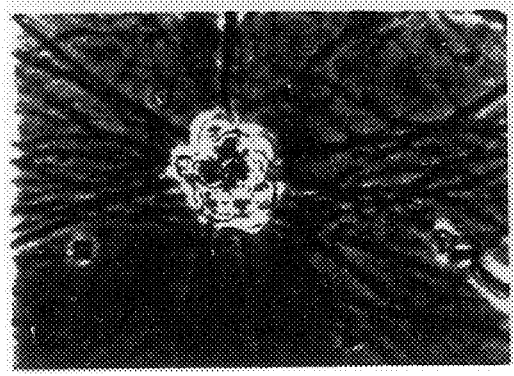
Figure 7D:
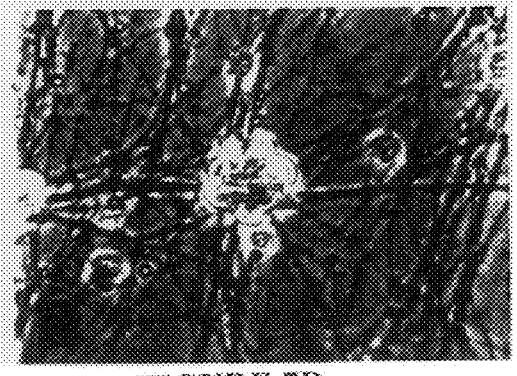
Figure 7E:
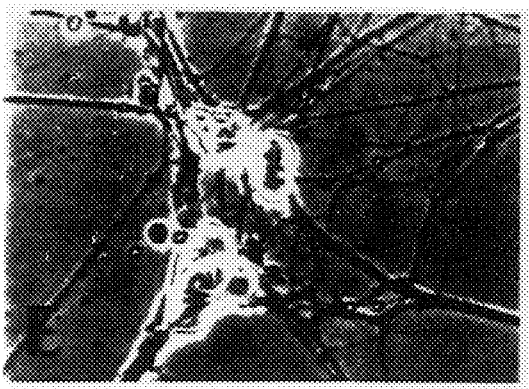
Figure 7F:
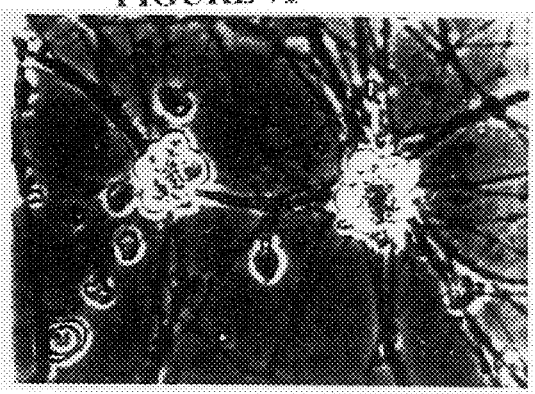

To extend the observations with post-mitotic PC12 cells, the efficacy of flavopiridol and olomoucine on sympathetic neurons deprived of NGF was evaluated. Sympathetic neurons were obtained from one-day-old rats and cultured in the presence of NGF for three days prior to NGF withdrawal. Typically after NGF deprivation, more than 80% of the neurons die within 48 hrs. Consistent with the observations with post-mitotic PC12 cells, both agents effectively inhibited death of the NGF-deprived neurons (FIGS. 6A, 6B, 6C, and 6D). Moreover, in accordance with the proposed involvement of inappropriate cell cycle entry in neuronal death, the dose response relationship for both compounds paralleled the ability of flavopiridol and olomoucine to inhibit thymidine incorporation in cycling PC12 cells (compare FIGS. 1A, 1B with FIGS. 6B, 6D). FIGS. 6A, 6B, 6C, and 6D also show that both drugs promoted good long-term survival of NGF-deprived neurons. At a concentration of 1 µM, flavopiridol promoted full survival for at least four days post-NGF depletion (FIG. 6A). Quantification at time periods longer than this was not possible since the neurons (which still appeared to be viable) tended to lift from the tissue culture dish in sheets. However, those neurons which remained in contact with the dish after this period maintained a viable appearance (FIGS. 7A, 7B, 7C, 7D, 7E, and 7F). Olomoucine (200 µM) also promoted long-term survival so that approximately 75% of the neurons were still viable by seven days post-NGF depletion. Again, quantitation of surviving neurons after this period was compromised by their losing contact with the tissue culture dish. In the cases of long-term cultures maintained with either flavopiridol or olomoucine, sheets of neuritic processes and healthy*appearing cell bodies were clearly visible floating in the medium. In contrast to olomoucine, iso-olomoucine was ineffective in promoting survival of NGF-deprived sympathetic neurons (FIG. 6C).

FIGS. 7A, 7B, 7C, 7D, 7E, and 7F illustrate the morphology of NGF-deprived neurons cultured with flavopiridol and olomoucine. It was previously noted that a number of agents that support the survival of such neurons do not maintain neurites and that these degenerate within several days (6,28). However, as shown in FIGS. 7A, 7B, 7C, 7D, 7E, and 7F, healthy processes are clearly visible in the drug-treated cultures six days after NGF depletion. In contrast, as with most other agents that rescue sympathetic neurons after NGF withdrawal, somatic hypertrophy was not maintained by the drugs (FIGS. 7A, 7B, 7C, 7D, 7E, and 7F).

Figure 8A:
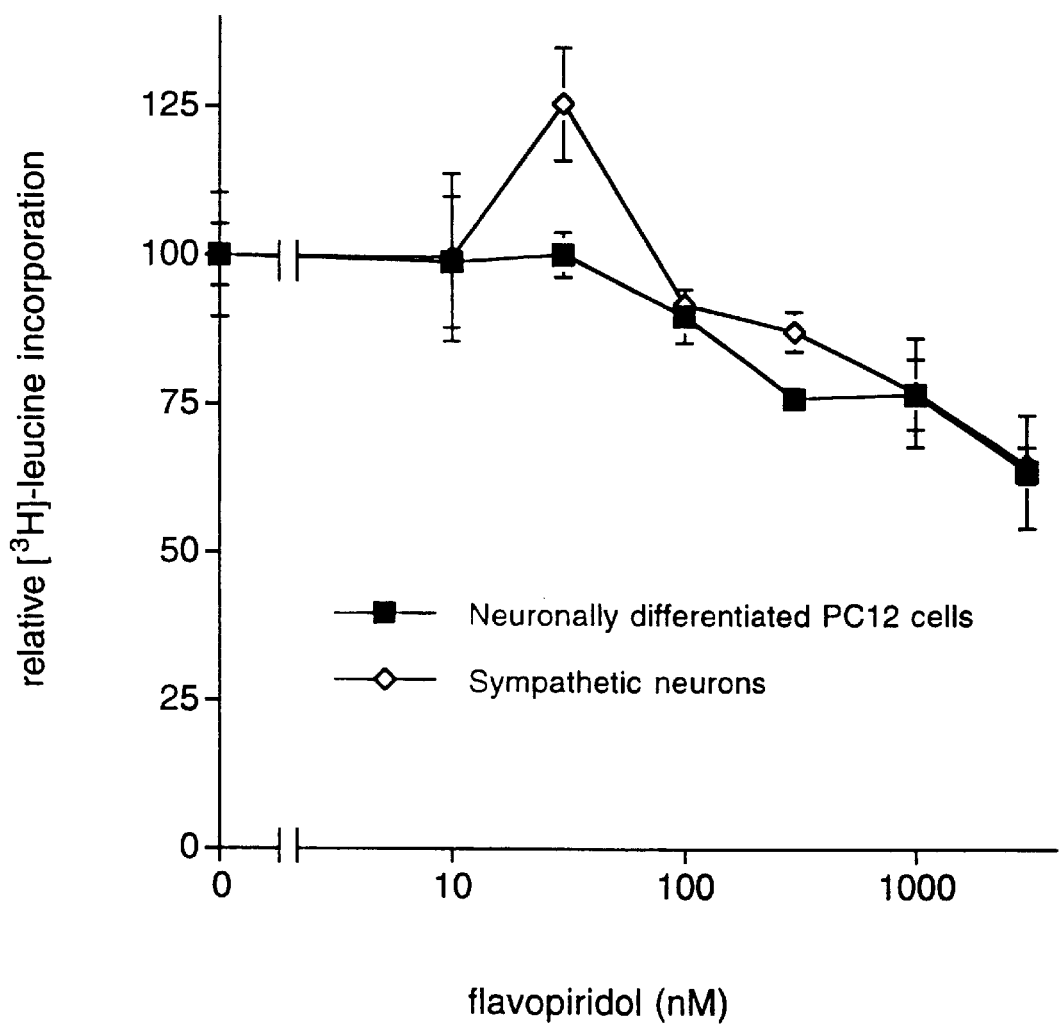
FIGS. 8A and 8B show the effects of flavopiridol (A) and olomoucine (B) on protein synthesis by neuronally-differentiated PC12 cells and rat primary sympathetic neurons. Data are expressed relative to untreated cultures. Each data point is the mean±SEM of 3 samples.
Figure 8B:
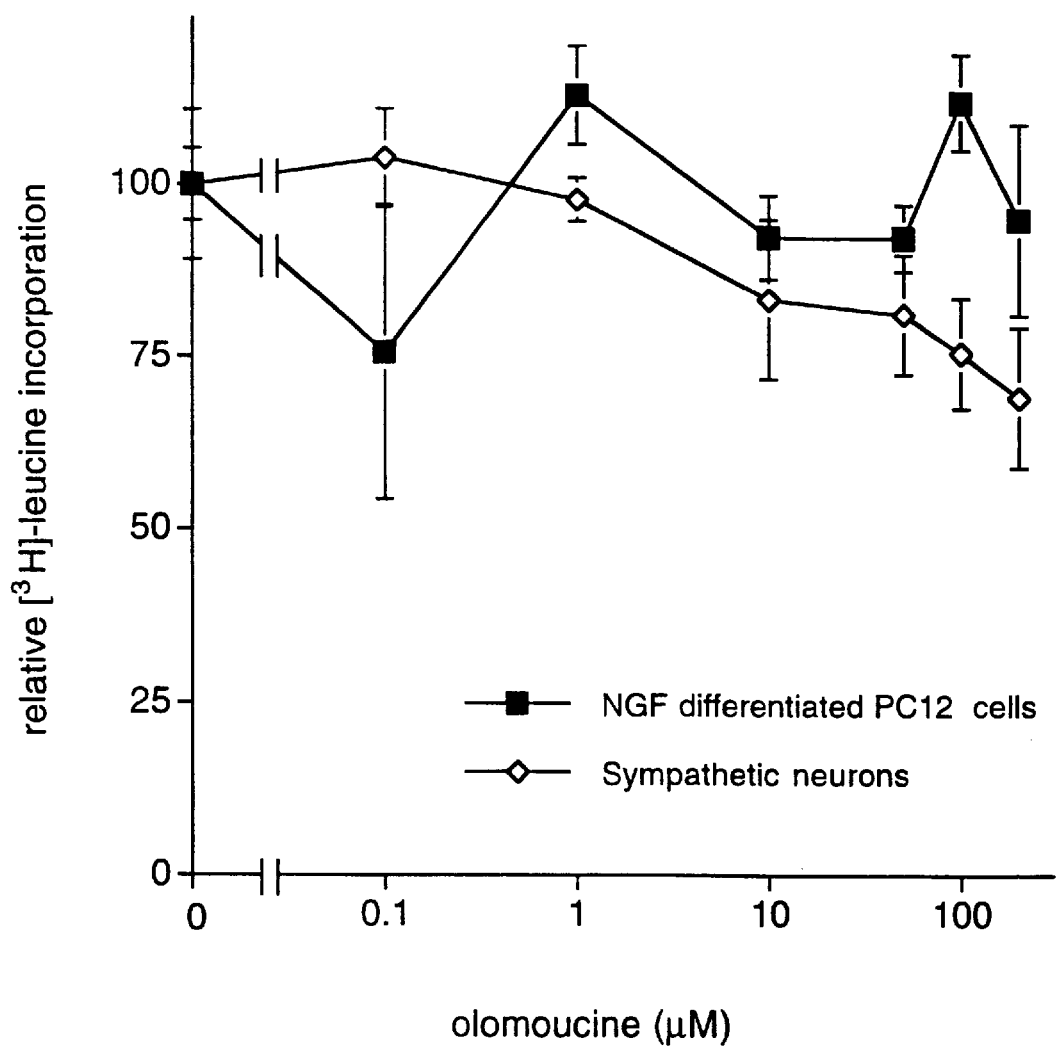

Because inhibition of protein synthesis promotes survival of neuronally differentiated PC12 cells and sympathetic neurons (11,14,23), we examined the effect of flavopiridol (FIG. 8A) and olomoucine (FIG. 8B) on leucine incorporation. As shown in FIG. 8A, 1 $\mu$M flavopiridol inhibited leucine incorporation by approximately 25% in cultures of either neuronally differentiated PC12 cells or sympathetic neurons. Olomoucine, (200 $\mu$M) inhibited leucine incorporation in sympathetic neuron cultures by approximately 30%, but had no effect on protein synthesis in PC12 cell cultures (FIG. 8B). Martin et al. (44) reported that at least 80% inhibition of protein synthesis is required to protect sympathetic neurons from NGF withdrawal. Accordingly, it is therefore unlikely that the mechanism by which flavopiridol and olomoucine rescue post-mitotic neurons and PC12 cells is by inhibition of protein synthesis.

Figure 9A:
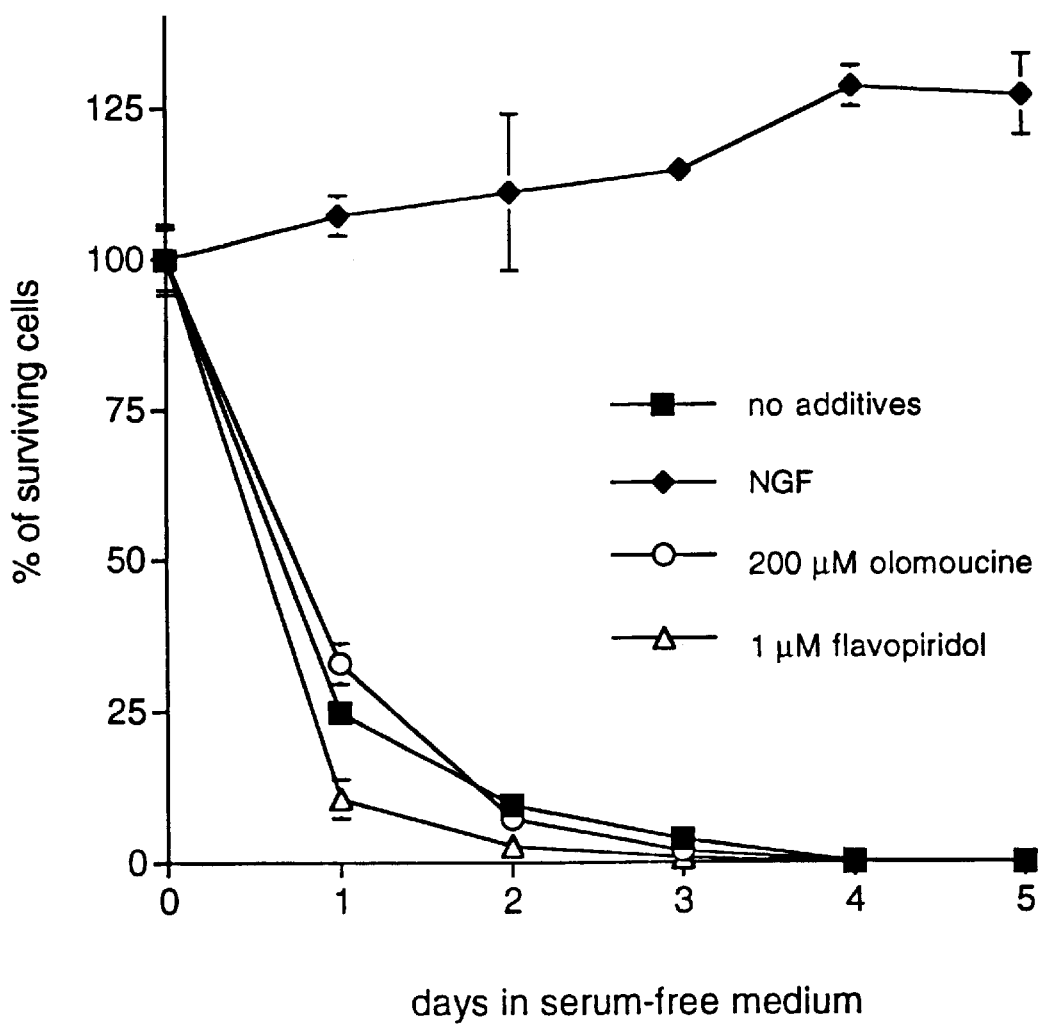
FIGS. 9A and 9B show that flavopiridol and olomoucine do not promote survival of naive PC12 cells following withdrawal of serum and also cause death in the presence of serum. (A) Replicate naive PC12 cell cultures were pre-incubated with or without the indicated inhibitor for 16 hr prior to withdrawal of serum and then treated for additional days as indicated. (B) Replicate naive PC12 cell cultures were grown as indicated in the presence of serum-containing RPMI 1640 medium without drug pretreatment and assessed at various times for numbers of live cells. Each data point is the mean±SEM of 3 samples.
Figure 9B:
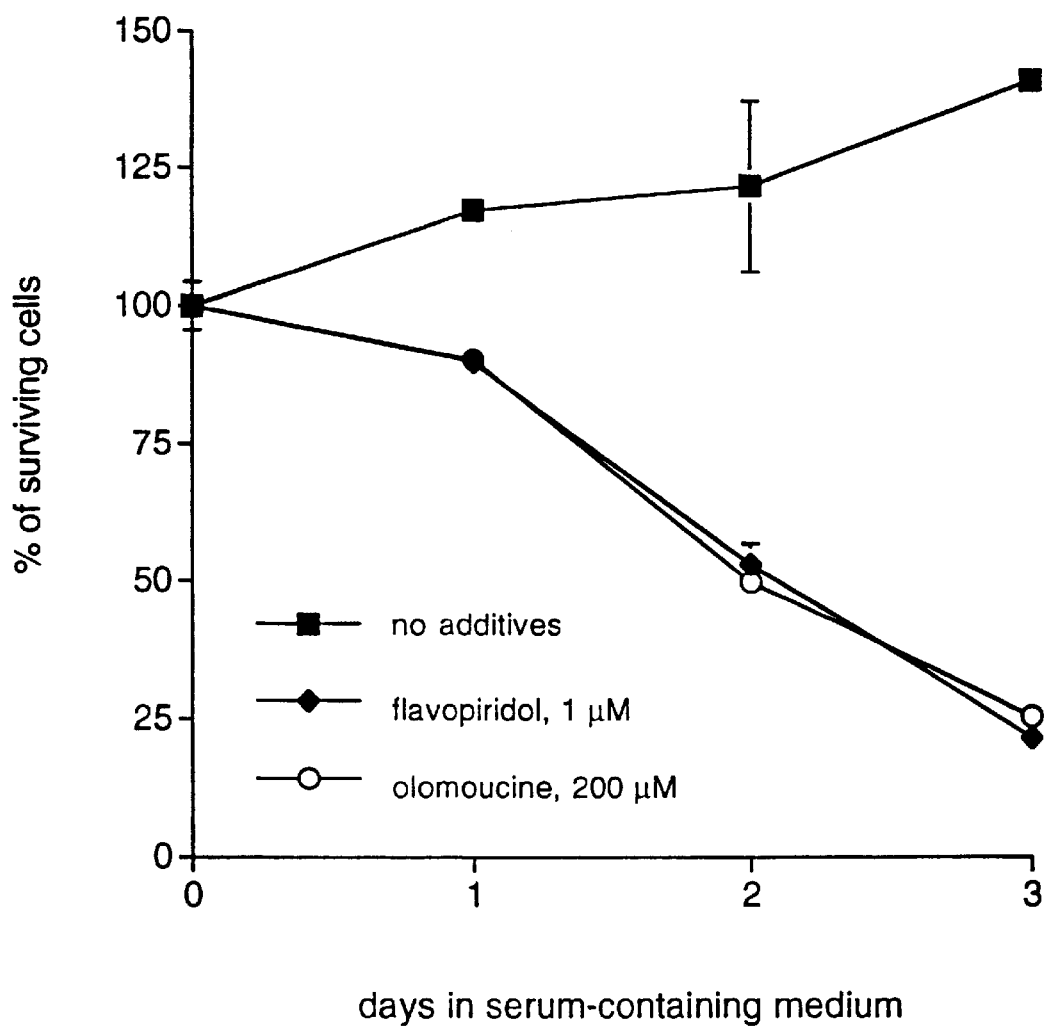

Flavopiridol and olomoucine do not promote survival of serum-deprived naive PC12 cells In contrast to their survival promoting effects on neuronally-differentiated PC12 cells and sympathetic neurons, flavopiridol and olomoucine failed to promote survival of naive PC12 cells deprived of trophic support by serum withdrawal. In order to insure that the naive PC12 cells were cell cycle arrested, naive PC12 cell cultures were pretreated with the cdk inhibitors for 16 hrs. Under these conditions, serum-deprived naive PC12 cells exposed to flavopiridol died somewhat more quickly than control cells without flavopiridol, whereas PC12 cells treated with olomoucine died at about the same rate as control cells (FIG. 9A). Naive cell cultures exposed to inhibitor only immediately following serum-deprivation (that is, without pretreatment) also showed no increased survival over control cells. Interestingly, flavopiridol and olomoucine proved to cause death of naive PC12 cells cultured in the presence of serum (75% death by day 3, see FIG. 9B). This level of death was considerably greater than the drugs evoked in cultures of post-mitotic neuronally-differentiated PC12 cells in the presence of NGF (approximately 20%death at day 3, see FIGS. 1B and 2B).

Discussion

It was hypothesized that trophic factors such as NGF prevent the death of proliferating neuroblasts by guiding them through the cell cycle, as is the case with naive PC12 cells, and inhibit the death of post-mitotic neurons by suppressing their inappropriate reentry into the cell cycle. Testing this model has involved examining whether agents which are known to prevent cell cycle progression promote neuronal survival. In previous studies, it was shown that multiple agents that induce cell cycle arrest such as N-acetylcysteine (28), chlorphenylthio-cAMP (33), as well as induction of dominant-negative ras (15), all suppress the death of neuronal cells caused by withdrawal of trophic support. Although these findings support the cell cycle/apoptosis model, the mechanisms by which such agents block the cell cycle remain largely unclear, and in each case, there was the possibility that alternative actions might be responsible for preventing death. To further and more directly evaluate the effects of cell cycle inhibition on death of neurons, two known inhibitors of the cell-cycle-related cdk family of kinases were employed.

Both flavopiridol and olomoucine suppressed the death of post-mitotic PC12 cells and sympathetic neurons caused by NGF deprivation. Significantly, the dose relationship for inhibition of thymidine incorporation by flavopiridol and olomoucine correlates very closely with their abilities to block cell death. In accordance with these observations, several lines of evidence support the potential role of cyclins and cdk's in the process of neuronal death. Brooks et al. (26) reported that elevated cdc2 activity is observed concurrent with NGF deprivation and death of neuronally-differentiated PC12 cells. In addition NGF treatment of PC12 cells leads to a reduction of both cdk2 and cdc2 activities (45) and increases the levels of p21, a G1 phase cdk inhibitor (46). Outside the nervous system, cdc2 activity has been shown to be required for lymphocyte granule protease mediated cell death (21). Furthermore, cyclin A induction and an increase in cyclin A/cdc2 activity occur in association with apoptosis induced pharmacologically or by myc-overexpression (47, 48).

Surprisingly, the cdk inhibitors were not effective in preventing the death of proliferation competent naive PC12 cells after withdrawal of trophic support. This is in sharp contrast to an earlier observations with other cell cycle blocking agents. The G1/S blockers as well as N-acetylcysteine are equally effective in protecting naive PC12 cells, post-mitotic neuronally-differentiated PC12 cells, and sympathetic neurons from loss of trophic support (28). This indicates that the manner in which cell cycle is blocked may be critical in determining whether an agent promotes neuronal survival. For instance, Gi blockers and not S, G2, or M-phase blockers promote survival of neuronal cells. This, however, does not imply that cells die in a cell-cycle stage specific manner, as Lindeboim et al. (49) has shown that apoptosis of PC12 cells occurs at each phase of the cell cycle.

It is possible that non-specific toxicity may negate any potential attenuation of cell death in naive PC12 cultures. The increased degree of cdk inhibitor-induced toxicity when compared to neuronal PC12 cells, however, suggests additional causes for this difference. One attractive explanation is that inhibition of cdk's in cycling PC12 cells forces a conflict between this aspect of cell cycle arrest and one or more endogenous proliferative signals. Naive PC12 cells, by origin, are transformed and therefore, must possess oncogenic signals that have yet to be defined. The cell cycle/apoptosis hypothesis would predict that the resulting conflict would lead to apoptotic death. In support of this view, flavopiridol promotes the death not only of naive PC12 cells but also of other transformed cell lines even in the presence of trophic support. After long-term exposure to NGF, PC12 cells attain a non-dividing phenotype lacking the oncogenic cue present in proliferating cultures and thereby eliminate the signaling conflict present in naive cultures.

The presently demonstrated effects of flavopiridol and olomoucine on survival are consistent with their ability to prevent cell cycle progression. Alternative actions could account for these observations. The most likely of these is the inhibition of kinases other than cdk's. For instance, as discussed above, olomoucine inhibits ERK's only somewhat less potently than cdk's. However, the data from this study, as well as that of Virdee and Tolkovsky (50) indicate that ERK's are not required for evocation or prevention of neuronal cell death. Another possibility is that these agents inhibit either the activation or activity of JNK family members. This possibility, however, does not appear to account for the differences observed here between post-mitotic and naive PC12 cells. In addition, this study shows that flavopiridol and olomoucine do not prevent the intracellular activation of JNK. While olomoucine does suppress JNK activity in vitro at concentrations similar to those at which it blocks death, flavopiridol proved to be a relatively poor inhibitor of JNK ($IC_{50}$>12 µM). Thus, it seems unlikely that inhibition of either JNK activation or activity accounts for the protective effects of flavopiridol or olomoucine.

In summary, this study shows that two distinct cdk inhibitors prevent the death of post-mitotic neuronal cells. Proliferating PC12 cells, however, were not saved by these agents. These results prove that conflicts between concurrent proliferative and non-proliferative signals may be one important factor in apoptosis due to trophic withdrawal.

References

1. Oppenheim, R. W. (1991) *Annu.Rev.Neurosci.* 14, 453–501.
2. Boniece, I. R., and Wagner, J. A. (1993) *J. Neurosci.* 13, 4220–4228.
3. Cheng, B., and Mattson, M. P. (1991). *Neuron.* 7, 10311041.
4. Greene, L. A., and Tischler, A. S. (1976) *Proc. Natl. Acad. Sci. USA* 73, 2424–2428.
5. Greene, L. A. (1978) *J. Cell Bio.,* 78, 747–755.
6. Bastitatou, A., and Greene, L. A. (1991) *J. Cell Bio.* 115, 461–471.
7. Levi-Montalcini, R., and Booker, B. (1960) *Proc. Natl. Acad. Sci. USA* 46, 384–391.
8. Gorin, P. D., and Johnson, E. M., Jr. (1979) *Proc. Natl. Acad. Sci. USA* 76, 5382–5386.
9. Gorin, P. D., and Johnson, E. M., Jr. (1980) *Brain Res.* 198, 27–42.
10. Levi-Montalcini, R., and Angeletti, P. U. (1963 ) *Dev. Biol.* 7, 653–659.
11. Martin, D., Schmidt, R., DiStefano, P., Lowry, O., Carter, J., and Johnson, E. M., Jr. (1988) *J. Cell Bio.* 106, 829–844.
12. Batistatou, A., and Greene, L. A. (1993) *J. Cell Biol.* 122, 523–532.
13. Edwards, S. N., Buckmaster, A. E., and Tolkovsky, A. M. (1991) *J. Neurochem.* 57, 2140–2143.
14. Pittman, R. N., Wang, S, DiBenedeto, A. J., and Mills, J. (1993) *J. Neurosci.* 13., 3669–3680.
15. Ferrari, G, and Greene, L. A. (1994) *EMBO J.* 13, 59225928.
16. Rubin, L. L., Philpott, K. L., and Brooks, S. F. (1993) *Curr. Biology* 3, 391–394.
17. Freeman, R. S. Estus, S., and Johnson, E. M., Jr. (1994) *Neuron* 12, 343–355.
18. Evan, G. E., Wyllie, A. H., Gilbert, C. S., Littlewood, T. D., Land, H., Brooks, M., Waters, C. M., Penn, L. Z., and Hancock, D. C. (1992) *Cell.* 69, 119–128.
19. Yonish-Rouach, E., Grunwald, D., Wilder, S., Kimchi, A., May, E., Lawrence, J., May, P., and Oren, M. (1993) *Mol. Cell Biol.* 13, 1415–1423.
20. Colombel, M., Olsson, C. A., Ng, P. Y. and Buttyan, R. (1992) *Cancer Res.* 52, 4313–4319.
21. Shi, L., Nishioka, W. K., Th'ng, J., Bradbury, E. M., Litchfield, D. W., and Greenburg, A. H. (1994) *Science* 263, 1143–1145.
23. Mesner, P. W., Winters, T. R., and Green, S. H. (1992) *J.Cell.Biol.* 119, 1669–1680.
24. Rukenstein, A. Rydel, R. E., and Greene, L. A. (1991) *J. Neurosci.* 11, 2552–2563.
25. Estus, S., Zaks, W. J., Freeman, R. S., Gruda, M., Bravo, R., and Johnson, E. M., Jr. (1994) *J. Cell Biol.* 127, 1717–1727.
26. Brooks, S. F., Gibson, A., and Rubin, L. L. (1993) *Soc. Neurosci. Abstr.* 19, 885.
27. Fedderson, R. M., Ehlenfeldt, R., Yunis, W. S., Clark, H. B., and Orr, H. T. (1992) *Neuron* 9, 955–966.
28. Ferrari, G., Yan, C. Y. I., and Greene, L. A. (1995) *J.Neurosci.* 15, 2857–2866.
30. van den Heuvel, S., and Harlow, E. (1993) *Science* 262, 2050–2054.
31. Pines, J. (1993) *TIBS* 18, 195–197.
32. Lee, V. M., Shelanski, M. L., and Greene, L. A. (1980) *Neuroscience* 5, 2239–2245.
33. Rydel, R. E., and Greene, L. A. (1988) *Proc. Natl. Acad. Sci USA* 85, 1257–1261.
34. Hibi, M., Lin, A., Smeal, T., Minden, A., and Karin, M. (1993) *Genes Dev.* 7, 2135–2148.
35. Losiewicz, M. D., Carlson, B. A., Kaur, G., Sausville, E. A., and Worland, P. J. (1994) *Bochem. Biophy, Res. Comm.* 201, 589–595.
36. Kaur, G., Stetler,-Stevenson, M., Sebers, S., Worland P., Sedlacek, H., Myers, C., Czech, J., Naik, R., and Sausville, E. (1992) *J. Natl. Cancer Inst.* 84, 17361740.
37. Vesely, J., Havlicek, L., Strnad, M., Blow, J. J., Donella-Deanna, A., Pinna, L., Letham, D. S., Kato, J., Detivaud, L., Leclerc, S., and Mieijer, L. (1994) *Eur. J. Biochem.* 224, 771–786.
38. Tsal, L., Delalle, I., Caviness, V. S., Chae, T., and Harlowe, E. (1994) *Science* 371, 419–423.
39. Lew, J., Huang, Q., Qi, Z., Winkfeln, R. J., Aebersold, R., Hunt, T., and Wang, J. H. (1994) *Science* 371, 423426.
40. Cowley, S., Paterson, H., Kemp, P., and Marshall, C. J. (1994) *Cell* 77, 841–852.
41. Pang, L., Sawada, T., Decker, S. J., and Saltiel, A. R. (1995) *J. Biol. Chem.* 270, 13585–13588.
42. Xia, Z., Dickens, M., Raingeaud, J., Davis, R. J., and Greenberg, M. E. (1996) *Science* 270, 1326–1331. i
43. Vojtek, A. B., and Cooper, J. A. (1995) *Cell* 82, 527–529.
44. Martin, D. P., Ito, A., Horigome, K., Lampe, P. A., and Johnson, E. M., Jr. (1992) *J. Neurobio.* 23, 1205–1220.
45. Buchkovich, K. J. and Ziff, E. B. (1994) *Mol. Bicl. Cell* 5, 1225–1241.
46. Yan, G -Z., and Ziff, E. B. (1995) *J. Neurosci.* 15, 6200–6212.
47. Meikrantz, W., Gisselbrecht, S., Tam, S. W., and Schlegel, R. (1994) *Proc. Natl. Acad. Sci. USA* 91, 3654–3758.
48. Hoang, A. T., Cohen, K. J., Barrett, J. F., Bergstrom, D. A. and Dang, C. V. (1994) *Proc. Natl. Acad. Sci. USA* 91, 6875–6879.
49. Lindenboim, L., Diamond, R., Rothenberg, E. and Stein, R. (1995) *Cancer Res.* 55, 1242–1247.
50. Virdee, K., and Tolkovsky, A. M. (1995) *Eur. J. Neurosci.* 7, 2159–2169.

What is claimed is:

1. A method of inhibiting death of post-mitotic neuronal cells in a subject comprising administering to the subject in need thereof an effective amount of an agent which prevents cell cycle progression and inhibits a cyclin dependent kinase so as to thereby inhibit the death of post-mitotic neuronal cells.

2. The method of claim 1, wherein the agent is flavopiridol, a salt of flavopiridol, olomoucine or a salt of olomoucine.

3. The method of claim 2, wherein the agent is flavopiridol or a salt thereof.

4. The method of claim 1, wherein the neuronal cell death is associated with neurological disorder selected from the group consisting of Parkinson's disease, amyotrophic lateral sclerosis, and Alzheimer's disease.

5. The method of claim 1, wherein the neuronal cell death is associated with a stroke.

6. The method of claim 1, wherein the subject is a human.

7. The method of claim 3, wherein the effective amount of flavopiridol or salt thereof is from about 5 mg/Kg of body weight to about 50 mg/Kg of body weight per day.

8. The method of claim 1, wherein the effective amount of flavopiridol or salt thereof is from about 10 mg/Kg of body weight to about 20 mg/Kg of body weight per day.

9. The method of claim 3, wherein the flavopiridol or salt thereof is administered orally, intervenously, subcutaneously, intravenously, subcutaneously, intramuscularly, topically, parenterally, by inhalation, rectally, or intraocularly.

10. A method of inhibiting death of post-mitotic neuronal cells in a subject comprising administering to the subject in need thereof an effective amount of flavopiridol or a salt thereof, thereby inhibiting the death of post-mitotic neuronal cells.

11. The method of claim 10, wherein the neuronal cell death is associated with neurological disorder selected from the group consisting of Parkinson's disease, amyotrophic lateral sclerosis, and Alzheimer's disease.

12. The method of claim 10, wherein the neuronal cell death is associated with a stroke.

13. The method of claim 10, wherein the subject is a human.

14. The method of claim 10, wherein the effective amount of flavopiridol or salt thereof is from about 5 mg/Kg of body weight to about 50 mg/Kg of body weight per day.

15. The method of claim 14, wherein the effective amount of flavopiridol or salt thereof is from about 10 mg/Kg of body weight to about 20 mg/Kg of body weight per day.

16. The method of claim 10, wherein the flavopiridol or salt thereof is administered orally, intervenously, subcutaneously, intravenously, subcutaneously, intramuscularly, topically, parenterally, by inhalation, rectally, or intraocularly.

* * * * *